United States Patent
Tada et al.

(10) Patent No.: US 11,191,562 B2
(45) Date of Patent: *Dec. 7, 2021

(54) MEDICAL DEVICE AND TREATMENT METHOD

(71) Applicant: TERUMO KABUSHIKI KAISHA, Tokyo (JP)

(72) Inventors: Yuichi Tada, Tokyo (JP); Mizuho Hirao, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 197 days.

This patent is subject to a terminal disclaimer.

(21) Appl. No.: 16/287,234

(22) Filed: Feb. 27, 2019

(65) Prior Publication Data

US 2019/0192185 A1 Jun. 27, 2019

Related U.S. Application Data

(63) Continuation of application No. PCT/JP2017/030368, filed on Aug. 24, 2017.

(30) Foreign Application Priority Data

Aug. 30, 2016 (JP) .............................. JP2016-167737

(51) Int. Cl.
*A61B 17/3207* (2006.01)
*A61B 17/32* (2006.01)

(52) U.S. Cl.
CPC .. *A61B 17/320758* (2013.01); *A61B 17/3207* (2013.01); *A61B 17/320708* (2013.01);

(Continued)

(58) Field of Classification Search
CPC .......... A61B 17/32053; A61B 17/3207; A61B 17/320708; A61B 17/320758;

(Continued)

(56) References Cited

U.S. PATENT DOCUMENTS 8,062,258 B2   11/2011   Demarais et al.
2004/0230212 A1   11/2004   Wulfman (Continued)

FOREIGN PATENT DOCUMENTS

JP   5636114 B2   12/2014
JP   2015-536802 A   12/2015
WO   2015120146 A1   8/2015

OTHER PUBLICATIONS

The extended European Search Report dated Mar. 31, 2020, by the European Patent Office in corresponding European Patent Application No. 17846295.8-1113. (7 pages).

(Continued)

*Primary Examiner* — Jocelin C Tanner
(74) *Attorney, Agent, or Firm* — Buchanan Ingersoll & Rooney PC

(57) ABSTRACT

A medical device to effectively remove an object, like an intravascular thrombus, in a body lumen includes: a rotatable tubular driving shaft; a cutting part that is provided on a distal side of the driving shaft, rotates together with the driving shaft, and cuts the thrombus; and a second cutting part that is disposed near the distal side of the driving shaft, inward of the cutting part.

21 Claims, 17 Drawing Sheets

(52) U.S. Cl.
CPC ............. *A61B 2017/320052* (2013.01); *A61B 2017/320064* (2013.01); *A61B 2217/005* (2013.01)

(58) Field of Classification Search
CPC .... A61B 17/32002; A61B 2017/00685; A61B 2017/22039; A61B 2017/320052; A61B 2017/320064; A61B 2017/320775; A61B 2017/320766; A61B 2017/320032; A61B 2017/320733; A61B 2017/320024; A61B 2217/005
See application file for complete search history.

(56) References Cited

U.S. PATENT DOCUMENTS

| | | | | |
|---|---|---|---|---|
| 2009/0018566 A1* | 1/2009 | Escudero | ....... | A61B 17/320758 606/159 |
| 2011/0301626 A1 | 12/2011 | To et al. | | |
| 2012/0109171 A1* | 5/2012 | Zeroni | ........... | A61B 17/320758 606/159 |
| 2013/0197395 A1* | 8/2013 | Janssens | ................ | A61B 10/02 600/567 |
| 2014/0163596 A1* | 6/2014 | Chen | .............. | A61B 17/320758 606/171 |
| 2014/0200438 A1 | 7/2014 | Millett et al. | | |
| 2014/0222045 A1* | 8/2014 | Schneider | ...... | A61B 17/320783 606/159 |
| 2014/0222048 A1* | 8/2014 | Ladd | ............. | A61B 17/320758 606/159 |
| 2016/0089171 A1* | 3/2016 | Honda | ................. | A61B 17/221 606/128 |
| 2017/0000518 A1* | 1/2017 | Smith | ............ | A61B 17/320758 |
| 2019/0262033 A1* | 8/2019 | Tada | ............... | A61B 17/320758 |

OTHER PUBLICATIONS

International Search Report (PCT/ISA/210) dated Nov. 7, 2017, by the Japanese Patent Office as the International Searching Authority for International Application No. PCT/JP2017/030368.

Written Opinion (PCT/ISA/237) dated Nov. 7, 2017, by the Japanese Patent Office as the International Searching Authority for International Application No. PCT/JP2017/030368.

Office Action (Decision of Refusal) dated Mar. 8, 2021, by the Japanese Patent Office in corresponding Japanese Patent Application No. 2018-537204 and an English Translation of the Office Action. (6 pages).

* cited by examiner

MEDICAL DEVICE AND TREATMENT METHOD

CROSS-REFERENCES TO RELATED APPLICATIONS

This application is a continuation of International Application No. PCT/JP2017/030368 filed on Aug. 24, 2017, and claims priority to Japanese Application No 2016-167737 filed on Aug. 30, 2016, the entire content of both of which is incorporated herein by reference.

FIELD OF THE INVENTION

The present invention generally relates to a medical device and a treatment method for cutting an object from an inner wall surface of a body lumen.

BACKGROUND DISCUSSION

Examples of a treatment method for treating a stenosed site caused by plaque, a thrombus, and the like in a blood vessel include a method of dilating the blood vessel by a balloon and a method of indwelling a mesh-like or coil-like stent in the blood vessel as a support for the blood vessel. However, it is difficult to carry out these methods to treat a stenosed site that is hardened due to calcification, and a stenosed site that occurs in a bifurcated portion of the blood vessel. Examples of a method that allows treatment in such cases include an atherectomy that cuts away stenotic matter such as a plaque or a thrombus.

An example of a device for performing atherectomy is disclosed in U.S. Pat. No. 8,062,258. This patent describes a catheter that is provided with a mechanism for conveying a cut object. This catheter includes an elongated rotation axis in the interior of a pipe body, and spiral-shaped concave and convex portions are formed on an outer circumference of the rotation axis. The rotation axis is rotatable in the interior of the catheter. When the rotation axis rotates in the catheter, an object located in the spiral-shaped concave portion is conveyed in the axis direction in the interior of the catheter while being pushed by the convex portion.

SUMMARY

When an object is conveyed by the catheter described in the above-noted U.S. patent, the object that receives a force from the rotation axis rotates in the interior of the catheter. Accordingly, the object in the interior of the catheter moves to the proximal side while drawing spirals in the interior of the catheter. Therefore, the conveyance distance of the object being conveyed in the interior of the catheter becomes long to decrease the conveyable amount.

A medical device and treatment method disclosed here can effectively remove an object in a body lumen.

The medical device according to according to one aspect comprises a rotatable tubular driving shaft positionable in the blood vessel, wherein the rotatable tubular driving shaft possesses a distal portion at a distal end of the rotatable tubular driving shaft; a cylindrically-shaped first cutting part configured to cut the object, with the cylindrically-shaped first cutting part being provided on the distal portion of the driving shaft so that the cylindrically-shaped first cutting part rotates together with the driving shaft; and a second cutting part configured to cut the object and being disposed adjacent the distal end of the rotatable tubular driving shaft and radially inward of the first cutting part.

According to another aspect, a medical device for removing an object in a body lumen comprises: a rotatable tubular driving shaft, a hollow first cutting part, and a second cutting part. The rotatable tubular driving shaft possesses a proximal end and an open distal end, with the rotatable tubular driving shaft including a lumen that extends between the proximal end and the open distal end of the rotatable tubular driving shaft. The first cutting part is fixed to the rotatable tubular driving shaft so that the first cutting part and the rotatable tubular driving shaft rotate together, and the first cutting part possesses a distal end portion at which is located an open distal end. The open distal end of the hollow first cutting part includes a sharp first cutting blade configured to cut the object when the object and the sharp first cutting blade are brought into contact with one another while the first cutting part is rotating together with the rotatable tubular driving shaft. The sharp first cutting blade extends distally beyond the open distal end of the rotatable tubular driving shaft, and the first cutting part possesses an inner surface surrounding an interior of the hollow first cutting part, with the interior of the first cutting part communicating with the lumen in the rotatable tubular driving shaft so that pieces of the object which have been cut by the sharp first cutting blade pass through the interior of the first cutting part and enter the lumen in the rotatable tubular driving shaft by way of the open distal end of the rotatable tubular driving shaft. The second cutting part is connected to the rotatable tubular driving shaft so that rotation of the rotatable tubular driving shaft results in rotation of the second cutting blade. The second cutting part includes a second cutting blade positioned in the interior of the hollow first cutting part so that the inner surface of the hollow first cutting part surrounds at least a portion of the second cutting part. The second cutting part possesses a distal end portion at which is located a sharp second cutting blade configured to cut the object when the object and the sharp second cutting blade contact one another while the second cutting part is rotating together with the rotatable tubular driving shaft.

According to another aspect, a treatment method for removing an object of a lesion area in a body lumen comprises: inserting a medical device into the body lumen, wherein the medical device comprises: a rotatable tubular driving shaft possessing a distal portion at a distal end of the rotatable tubular driving shaft; a cylindrically-shaped first cutting part provided on the distal portion of the driving shaft so that the cylindrically-shaped first cutting part rotates together with the driving shaft, and a second cutting part disposed adjacent the distal end of the rotatable tubular driving shaft and radially inward of the first cutting part. The method also comprises: cutting the object in the body lumen by rotating the first cutting part and the second cutting part through rotation of the driving shaft to produce a cut object, and guiding the cut object to a lumen of the rotating driving shaft; conveying the cut object in the lumen of the rotating driving shaft toward a proximal end of the rotating driving shaft; and extracting the medical device from the body lumen.

The medical device and the treatment method configured as the above can smoothly guide the object cut by the first cutting part and the second cutting part to the lumen of the driving shaft that rotates together with the cutting part. In this process, the cutting part and second cutting part having different characteristics cut the thrombus, so that it is possible to effectively cut and remove the object in the body lumen.

BRIEF DESCRIPTION OF THE DRAWINGS

FIG. 4(B) is a cross-sectional view along an IVB-IVB line in FIG. 4(A).

DETAILED DESCRIPTION

Figure 1:
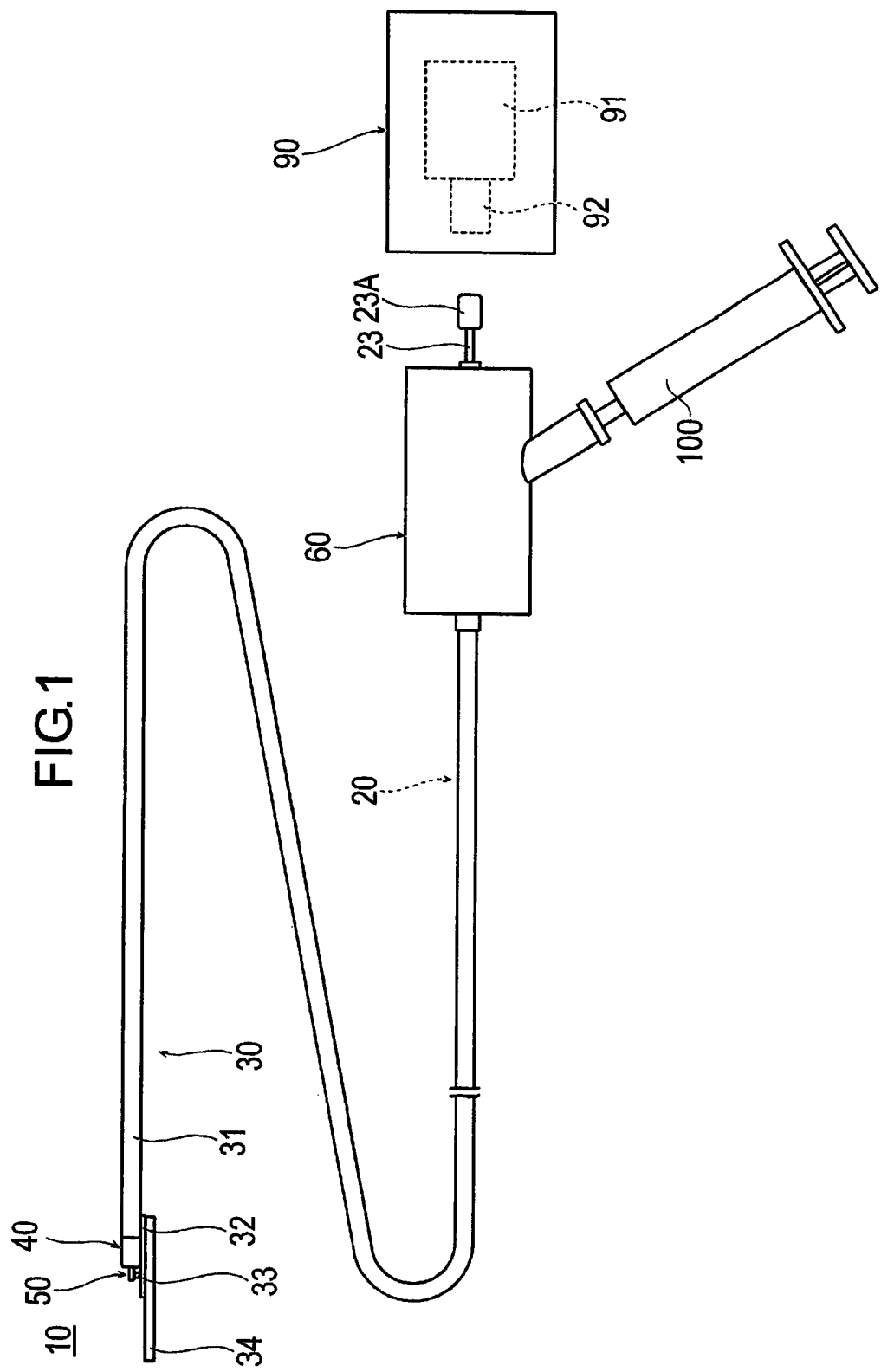
FIG. 1 is a plan view illustrating a medical device according to a first embodiment.

Hereinafter, with reference to the drawings, embodiments of the medical device and method, representing examples of the disclosed medical device and method, will be described. Note that, the size ratio in the drawings may be exaggerated for convenience of explanation, and may be different from the actual ratio in some cases.

First Embodiment

A medical device 10 according to a first embodiment is a medical device configured to be inserted into a blood vessel and is used in a treatment of destroying and removing a thrombus, in acute limb ischemia and deep venous thrombosis. In the present description, a side or end of the device to be inserted into the blood vessel is referred to as the "distal side" or "distal end", and a hand-side where the device is operated is referred to as the "proximal side" or "proximal end". An object to be removed is not necessarily limited to a thrombus, a plaque, and a calcified lesion. All objects that can exist in a body lumen can be objects to be removed using the medical device and method disclosed here.

Figure 2:
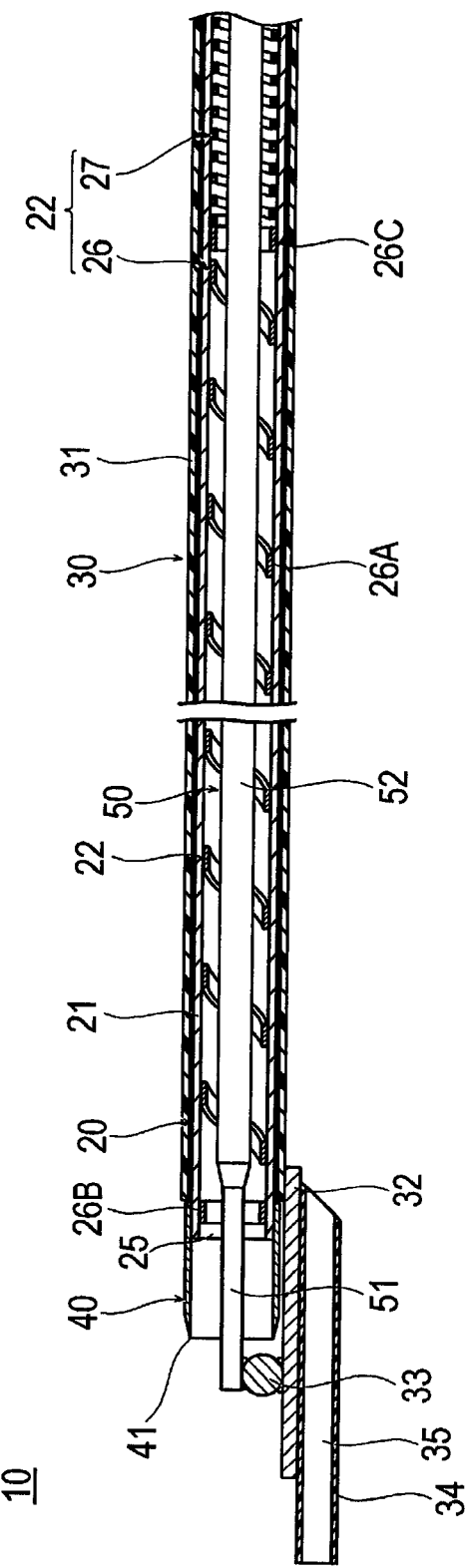
FIG. 2 is a cross-sectional view illustrating a distal portion of the medical device.
Figure 3:
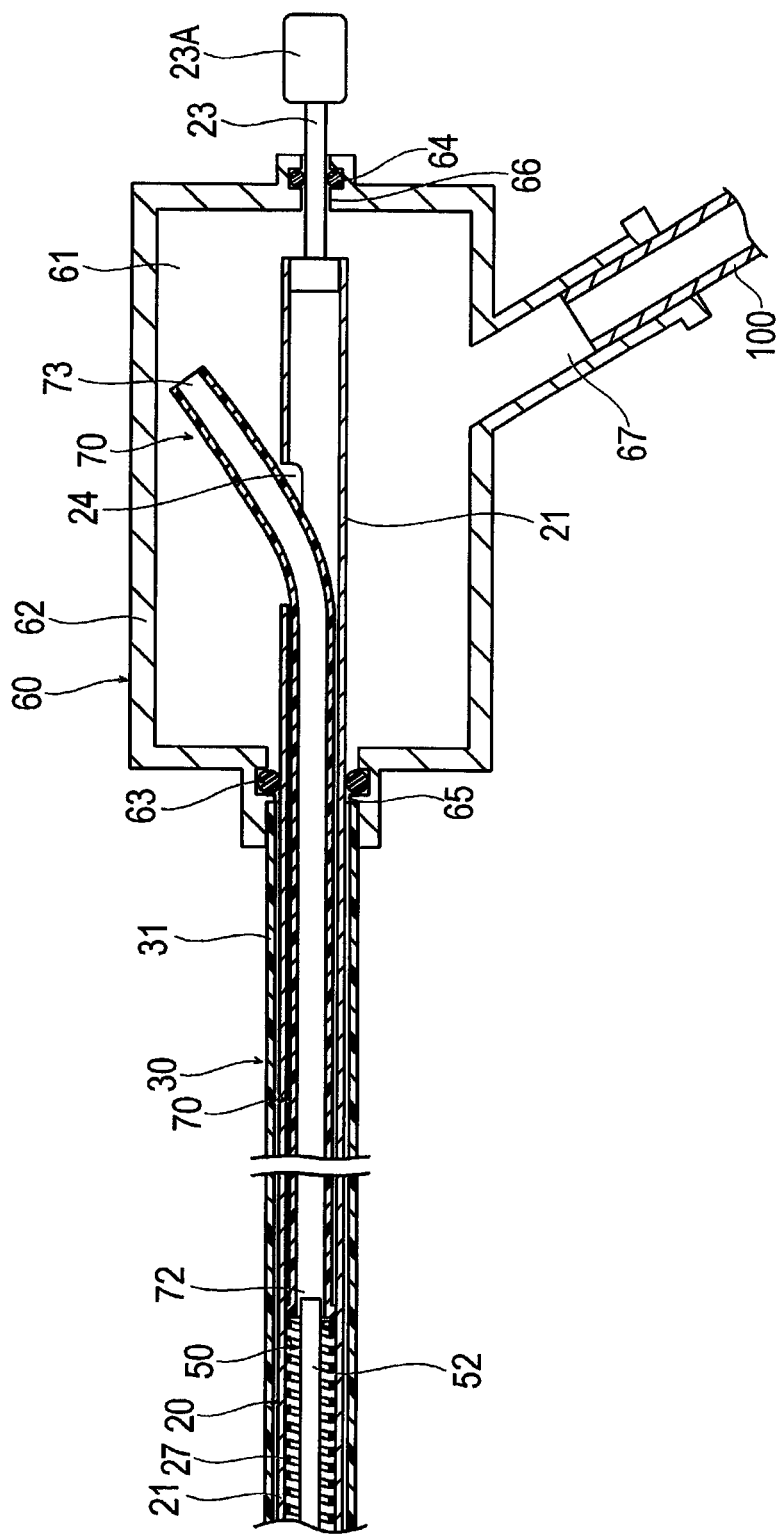
FIG. 3 is a cross-sectional view illustrating a proximal portion of the medical device.
Figure 4:
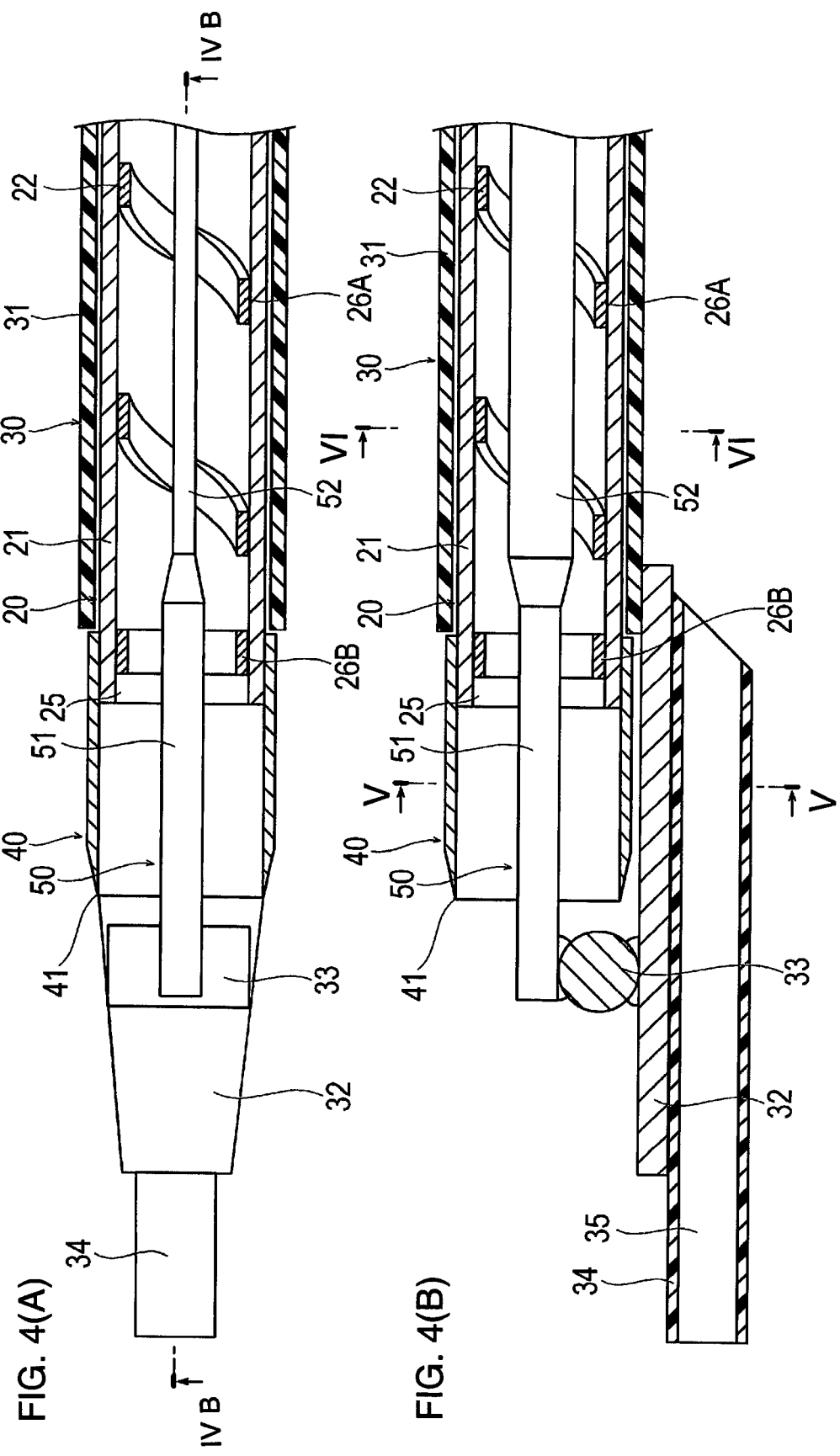
FIGS. 4(A) and 4(B) depict views illustrating the distal portion of the treatment device, with FIG. 4(A) being a cross-sectional view.
Figure 5:
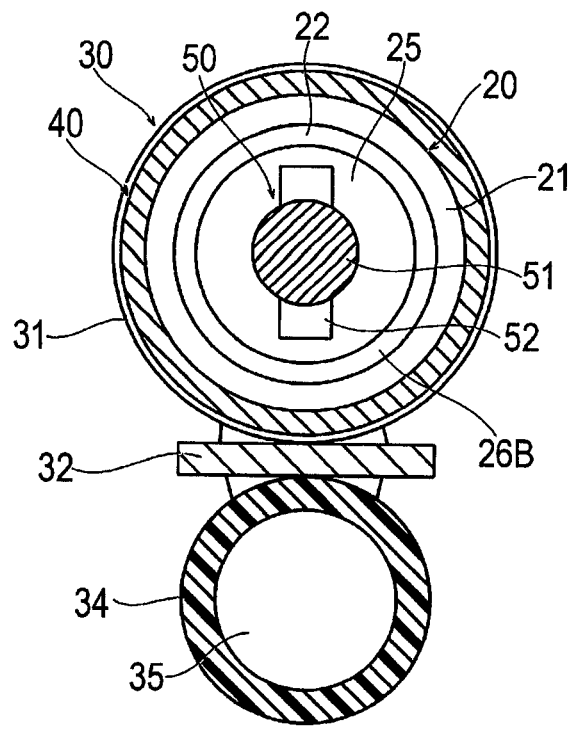
FIG. 5 is a cross-sectional view along a B-B line in FIG. 4(B).
Figure 6:
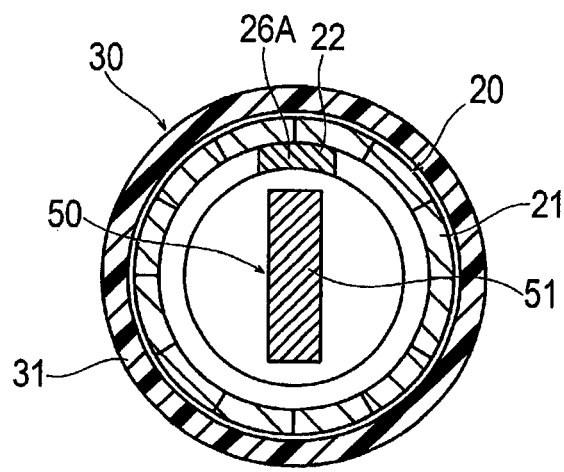
FIG. 6 is a cross-sectional view along a VI-VI section line in FIG. 4(B).
Figure 7:
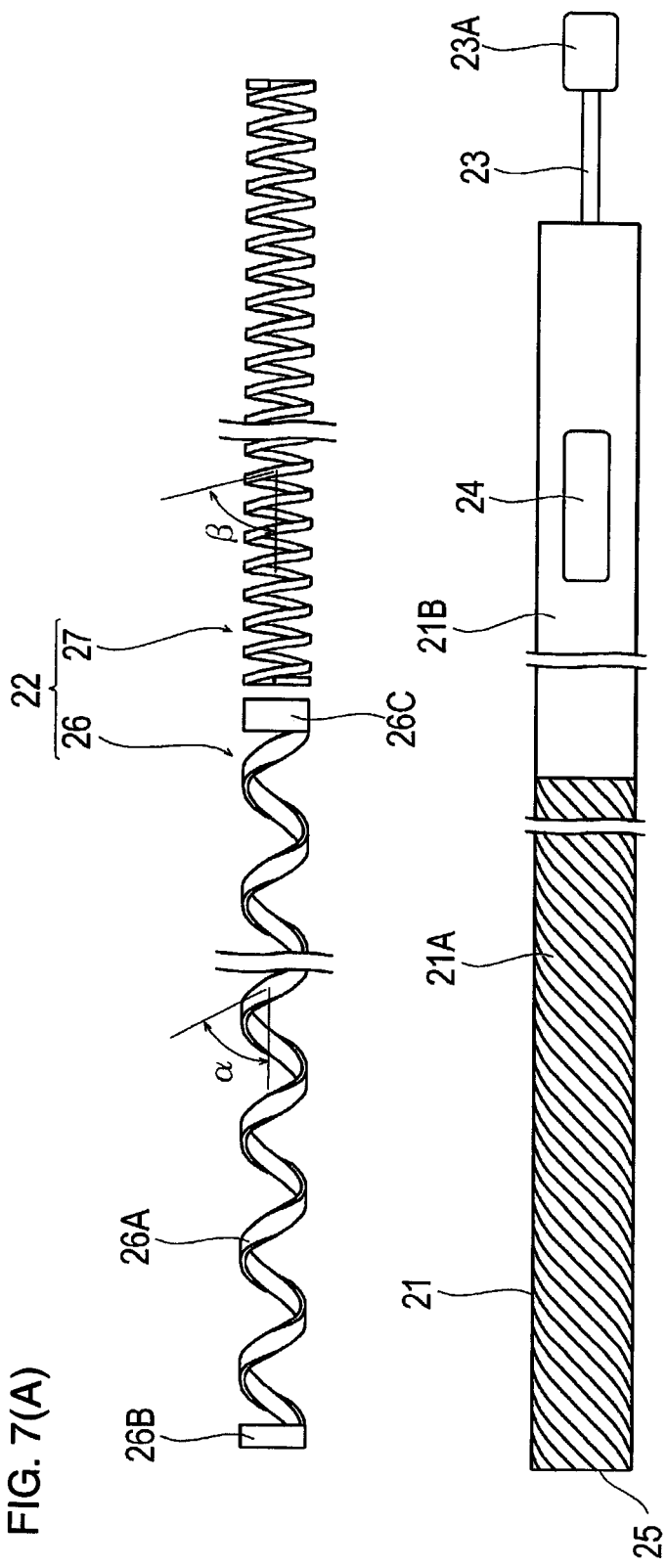
FIG. 7(A) is a plan view of a carrier and FIG. 7(B) is a plan view illustrating a driving shaft.
Figure 8:
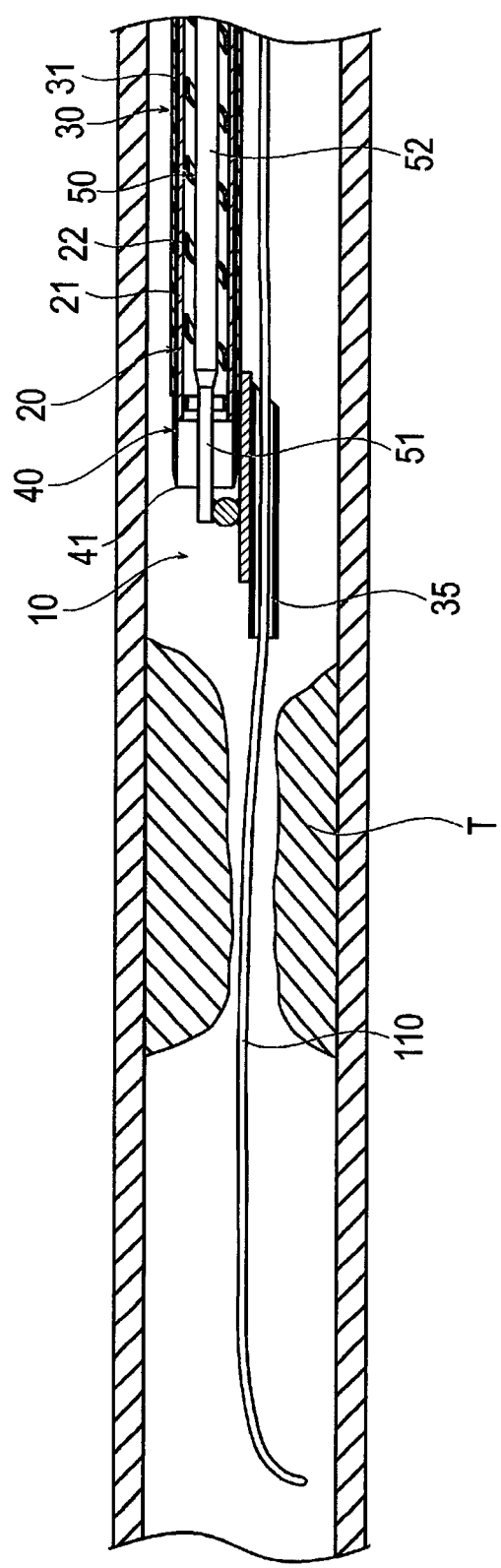
FIG. 8 is a cross-sectional view illustrating a state where the medical device is inserted into a blood vessel.

The medical device 10 is provided with, as illustrated in FIGS. 1 to 3, an elongated driving shaft 20 that is rotationally driven, an outer tube 30 that contains the driving shaft 20 (the driving shaft 20 is positioned in the outer tube 30), a cutting part 40 that cuts a thrombus, and a resistive body 50 that is disposed in the driving shaft 20. The medical device 10 is further provided with an operation unit 60 that is provided on a proximal side end portion of the outer tube 30, a rotary drive unit 90 that rotates the driving shaft 20, an aspiration pipe body 70 that is interlocked with the driving shaft 20 in an interior of the operation unit 60, and a syringe 100 that is connected to the operation unit 60.

The driving shaft 20 is a part for transmitting a rotation force to the cutting part 40, and conveying an object that enters a lumen of the driving shaft 20 to the proximal side or in the proximal direction. The driving shaft 20 is provided with, as illustrated in FIGS. 2 to 7, an elongated tubular driving tube 21, a spiral-shaped carrier 22 that is provided on an inner peripheral surface of the driving tube 21, and a connection shaft 23 that connects the driving tube 21 to the rotary drive unit 90.

The driving tube 21 penetrates through the outer tube 30, and has a distal portion to which the cutting part 40 is fixed. A proximal portion of the driving tube 21 is located in an accommodation space 61 in the interior of the operation unit 60. The driving tube 21 is rotationally driven by the rotary drive unit 90 via the connection shaft 23. The driving tube 21 includes a leading-out hole 24 on a side surface of the proximal portion located in the accommodation space 61. The driving tube 21 includes an inlet part 25 into which a thrombus enters, in a distal side end portion of the driving tube 21. In a proximal side end portion of the driving tube 21, the lumen is blocked and the connection shaft 23 is fixed. The leading-out hole 24 is an outlet from which the thrombus having been entered an interior of the driving tube 21 from the inlet part 25 is discharged.

The driving tube 21 is flexible, and has a characteristic capable of transmitting the power of rotation that is applied from the proximal side to the distal side. The driving tube 21 includes, for example, a distal side driving tube 21A in which multiple wires are arranged and interlocked by being wound in a spiral shape, and a proximal side driving tube 21B that is a pipe body or tubular body interlocked with a proximal side of the distal side driving tube 21A (see FIG. 7(B)). The distal side driving tube 21A has a slit (space) between adjacent wires that penetrates from an inner peripheral surface of the distal side driving tube 21A to an outer peripheral surface of the distal side driving tube 21A. The winding direction of the spiral of the wires is preferably a reverse direction of the winding direction of the spiral of the carrier 22, but is not limited thereto. When the winding direction of the spiral of the wires is a reverse direction of the winding direction of the spiral of the carrier 22, the different spirals are reinforced with each other to improve the intensity or strength and to reduce the anisotropy of operations, thereby improving the operability. The configuration of the driving tube is not specially limited. For example, the driving tube may be a pipe body or tubular body in which spiral-shaped slits are formed by laser processing or the like.

As for the constituent material for the driving tube 21, for example, stainless steel, Ta, Ti, Pt, Au, W, polyolefin such as polyethylene or polypropylene, polyester such as polyamide or polyethylene terephthalate, fluorinated polymers such as ETFE, PEEK (polyether ether ketone), and polyimide, can be used suitably. Moreover, the constituent material for the driving tube 21 may include multiple materials, or a reinforcing member such as a wire may be embedded in the material forming the driving tube.

The inside diameter of the driving tube 21 can be set as appropriate, and is 0.5 to 3.0 mm, for example. The outside diameter of the driving tube 21 can be set as appropriate, and is 0.8 to 4.0 mm, for example. The length of the driving tube 21 in the axial direction can be set as appropriate, and is 150 to 2000 mm, for example.

The connection shaft 23 includes a distal side end portion, which is fixed to the driving tube 21. The connection shaft 23 includes an interlock axis 23A on the proximal side that is interlocked with the rotary drive unit 90 and receives the power of rotation. A constituent material for the connection shaft 23 is not specially limited as long as the rotation power can be transmitted, and is stainless steel, for example. The rotary drive unit 90 may be directly connected to the driving tube 21. In that case, the proximal side of the driving tube 21 may include a notch, and the notch may be interlocked with the rotary drive unit 90. In this process, the lumen on the proximal side of the driving tube 21 is sealed with the leading-out hole 24.

The carrier 22 is a spiral-shaped part that is provided on the inner peripheral surface of the driving tube 21, and is rotationally driven by the driving tube 21. The carrier 22 rotates to cause a force directed toward the proximal side or proximal end to act on a thrombus having entered the lumen of the driving tube 21, and to move the thrombus to the proximal side or in the proximal direction. Moreover, the lumen of the driving tube 21 also has a role as a lumen for causing an aspiration force acting from the proximal side to act on the distal side. As shown in FIGS. 2 and 7(A), the carrier 22 includes a first carrier (first carrier part) 26 that is disposed in the interior of the distal portion of the driving tube 21, and a second carrier (second carrier part) 27 that is disposed closer to the proximal side than the first carrier 26 in the interior of the driving tube 21. The first carrier 26 has an inter-pitch distance of the spiral (the axial distance or pitch between adjacent windings of the spiral) longer than that of the second carrier 27. The inter-pitch distance is a distance in the axial direction when the spiral is wound at 360 degrees in the circumferential direction. The first carrier 26 having an inter-pitch distance longer than that of the second carrier 27 allows a long distance for conveyance by one rotation, and thus has a large amount of conveyance of the thrombus. Accordingly, the first carrier 26 having a relatively longer inter-pitch distance is provided in the distal portion of the driving tube 21 to allow the lumen on an inlet side (distal side) into which the thrombus enters to be maintained all the time in a state where the lumen is not clogged by the thrombus. In addition, the first carrier 26 having such a relatively longer inter-pitch distance receives a large reaction force received from the thrombus being conveyed, and is required to have sufficient strength (i.e., the first carrier should be able to withstand the reaction force). Accordingly, in the present embodiment, the first carrier 26 is manufactured by laser processing but is not a coil in which the wires are wound. The first carrier may be manufactured by winding the wires as long as the first carrier can secure or exhibit sufficient strength (i.e., withstand the reaction force) and is rotatable in the outer tube 30. Alternatively, the carrier 22 includes the second carrier 27 that is disposed in the interior of the distal portion of the driving tube 21, and the first carrier 26 that is disposed closer to the proximal side than the second carrier 27 in the interior of the driving tube 21. Accordingly, the second carrier 27 having a distance between pitches shorter than that of the first carrier 26 is located on the distal side. This makes the distal portion of the driving shaft 20 flexible, thereby improving the accessibility of the medical device 10 to an object to be cut.

The first carrier 26 includes a spiral-shaped spiral part 26A, a distal side ring part 26B that is located on a distal side from the spiral part 26A, and a proximal side ring part 26C that is located on a proximal side from the spiral part 26A. Each of the distal side ring part 26B and the proximal side ring part 26C is a pipe body or tubular body that is continuous over 360 degrees. The first carrier 26 is fixed to the inner peripheral surface of the driving tube 21 with the distal side ring part 26B and the proximal side ring part 26C so that rotation of the diving tube 21 results in rotation of the first carrier 26, the distal side ring part 26B and the proximal side ring part 26C. The first carrier 26 is fixed with respect to the driving tube 21 by welding or bonding, for example. Alternatively, the first carrier 26 may be fixed with respect to the driving tube 21 by fitting (frictional force). The first carrier 26 is partially fixed with respect to the driving tube 21, so that a portion being not fixed (the spiral part 26A in the present embodiment) can be flexibly deformed. This allows the first carrier 26 to temporarily deform by a force received from a thrombus being conveyed, so that the breakage can be suppressed. Note that, the fixed position and the number of fixed places of the first carrier 26 relative to the driving tube 21 are not specially limited. For example, the entire outer peripheral surface of the first carrier 26 may be fixed to the driving tube 21. Alternatively, only either one of the distal side and the proximal side of the first carrier 26 may be fixed to the driving tube 21. The inside diameters and the outside diameters of the spiral part 26A, the distal side ring part 26B, and the proximal side ring part 26C are equal to one another. The distal side ring part 26B and the proximal side ring part 26C provide a smooth inner peripheral surface over 360 degrees at end portions of the first carrier 26. Accordingly, the distal side ring part 26B and the proximal side ring part 26C come into smooth contact with but do not interfere with the resistive body 50 that is located in the interior and relatively rotates, so that the breakage can be suppressed. No distal side ring part 26B may be provided. In this case, the spiral-shaped spiral part 26A further extends in a spiral shape toward the distal side. In this case, the vicinity of a distal side end portion of the spiral-shaped spiral part 26A is joined to the driving tube 21 by welding or the like. This can reduce the occupied volume of the first carrier 26, and increase a space in the lumen of the driving shaft 20. Accordingly, it is possible to more smoothly guide many objects into the lumen of the driving shaft 20, and convey the objects. When the spiral-shaped spiral part 26A constitutes the distal side end portion of the first carrier 26, the distal side end portion of the spiral part 26A is disposed near a position of a distal side end portion of the cutting part 40. This can continuously guide the objects cut by the cutting part 40 to the spiral part 26A. Accordingly, a thrombus T is easily sent to the proximal side in the lumen of the driving shaft 20, and the lumen is not so likely to become clogged.

The second carrier 27 is a spiral-shaped member having an inter-pitch distance (the distance or pitch between adjacent windings of the spiral) shorter than that of the first carrier 26. The second carrier 27 is a coil, for example. Parts (for example, a distal side end portion and a proximal side end portion) of the second carrier 27 are fixed to the inner peripheral surface of the driving tube 21. The second carrier 27 is fixed with respect to the driving tube 21 by welding or bonding, for example. Alternatively, the second carrier 27 may be fixed with respect to the driving tube 21 by fitting (frictional force). The second carrier 27 is partially fixed with respect to the driving tube 21, so that a portion which is not fixed can be flexibly deformed. This allow the second carrier 27 to be temporarily deformed by a force received from a thrombus being conveyed, so that breakage can be suppressed. The fixed position and the number of fixed places of the second carrier 27 relative to the driving tube 21 are not specially limited. For example, the entire outer peripheral surface of the second carrier 27 may be fixed to the driving tube 21. Alternatively, only either one of the distal side and the proximal side of the second carrier 27 may be fixed to the driving tube 21. The second carrier 27 that is a coil is easily manufactured although it is long, so that the cost can be reduced. Moreover, the second carrier 27 that is a coil is easily inserted into the interior of the driving tube 21 and disposed. The shape of a cross section perpendicular to the central axis of the second carrier 27 (the shape of the inner periphery of the second carrier 27) is not specially limited, but may be a square, a rectangle, a parallelogram, a trapezoid, a circle, or an ellipse, for example.

Constituent materials for the first carrier 26 and the second carrier 27 preferably have sufficient strength to allow an object to be conveyed, and for example, a shape memory alloy to which the shape memory effect and the super elasticity are assigned by thermal treatment, stainless steel, Ta, Ti, Pt, Au, W, polyolefin such as polyethylene or polypropylene, polyester such as polyamide or polyethylene terephthalate, fluorinated polymers such as ETFE, PEEK (polyether ether ketone), and polyimide, can be used suitably. As for the shape memory alloy, a Ni-Ti-based, Cu-Al-Ni-based, or Cu-Zn-Al-based alloy, any combination thereof, or the like is preferably used. When the first carrier 26 and the second carrier 27 are made of a shape memory alloy, the first carrier 26 and the second carrier 27 can be excellently returned to original shapes after having temporarily deformed by a reaction force received from the thrombus, and thus can maintain the function while suppressing the breakage. The constituent materials for the first carrier 26 and the second carrier 27 may be different from each other.

An inclined angle $\alpha$ of the spiral relative to the central axis of the first carrier 26 can be set as appropriate, and is, for example, 10 to 75 degrees, preferably 15 to 40 degrees, and more preferably 25 to 35 degrees. An inclined angle $\beta$ (torsion angle) of the spiral relative to the central axis of the second carrier 27 is larger than the inclined angle $\alpha$ of the spiral of the first carrier 26, and is, for example, 25 to 80 degrees, preferably 30 to 60 degrees, and more preferably 35 to 45 degrees. The large inclined angle results in the short inter-pitch distance and the short conveyance distance by one rotation, however, can reduce a force necessary for conveyance and suppress breakage, thereby improving safety. The small inclined angle results in the long inter-pitch distance and the long conveyance distance by one rotation, however, a force necessary for conveyance becomes large, and enhancing the rigidity and the flexibility is required in order to suppress the breakage.

The inside diameters of the first carrier 26 and the second carrier 27 can be selected as appropriate, and may be 0.4 to 2.8 mm, for example. The outside diameters of the first carrier 26 and the second carrier 27 preferably have a prescribed clearance with respect to the inner peripheral surface of the driving tube 21 such that the first carrier 26 and the second carrier 27 can come into contact with an inner wall surface of the driving tube 21, and can be inserted into the driving tube 21. The outside diameters of the first carrier 26 and the second carrier 27 are 0.49 to 2.99 mm, for example. The inside diameter of the first carrier 26 may be different from the inside diameter of the second carrier 27. Moreover, the outside diameter of the first carrier 26 may be different from the outside diameter of the second carrier 27.

The length of the first carrier 26 in the axis direction can be selected as appropriate, and is 5 to 300 mm, for example. The length of the second carrier 27 in the axis direction can be selected as appropriate, and is 301 to 1995 mm, for example. The carrier 22 may include only the first carrier 26. In that case, the length of the first carrier 26 in the axis direction may be 1 to 2000 mm.

The outer tube 30 is provided with an outer sheath 31 that rotatably contains the driving shaft 20, an extension part 32 that is fixed to an outer peripheral surface of a distal portion of the outer sheath 31, a fixing part 33 that fixes the extension part 32 and the resistive body 50, and a tip tube 34 that is fixed to the extension part 32.

The outer sheath 31 is a tubular body, and includes a proximal side end portion, which is fixed to the operation unit 60. The distal side end portion of the outer sheath 31 is positioned on a proximal side of the cutting part 40. A cross-sectional area of a gap between the outer sheath 31 and the driving tube 21 is preferably sufficiently smaller than a cross-sectional area in an interior of the aspiration pipe body 70. This can suppress an aspiration force that acts on the interior of the driving tube 21 from the aspiration pipe body 70 from diffusing in a space between the outer sheath 31 and the driving tube 21 through slits between the wires of the driving tube 21.

The extension part 32 is fixed to a part of the outer peripheral surface of the distal portion of the outer sheath 31, and extends closer to the distal side than the outer sheath 31. The extension part 32 is a member for fixing the resistive body 50 and the tip tube 34 with respect to the outer sheath 31. The extension part 32 is provided only to a part in the circumferential direction of the outer peripheral surface of the outer sheath 31 so as not to hinder the cutting part 40 from cutting a thrombus. That is, the extension part 32 has a limited circumferential extent less than 360°. The extension part 32 is a plate material, for example, but may be a wire, for example, because the shape thereof is not limited.

The fixing part 33 is a member for fixing a part on a distal side of the extension part 32 to the resistive body 50. The fixing part 33 is located closer to the distal side than the cutting part 40 of the extension part 32. The fixing part 33 plays a role in bridging a distance between the extension part 32 and the resistive body 50 that are located away from each other. Accordingly, the fixing part 33 has a size that allows the resistive body 50 to be disposed to a suitable position with respect to the extension part 32. The fixing part 33 is a wire, for example, but the shape thereof is not limited. The fixing part 33 may be integrally configured with the extension part 32 and the resistive body 50, for example.

The tip tube 34 is fixed to the extension part 32. The tip tube 34 includes a guide wire lumen 35 into which a guide wire can be inserted.

A constituent material for the outer sheath 31 is not specially limited, and for example, polyolefin such as polyethylene or polypropylene, polyester such as polyamide or polyethylene terephthalate, or various kinds of elastomers, fluorinated polymers such as ETFE, PEEK (polyether ether ketone), and polyimide, can be used suitably. Moreover, the outer sheath 31 may include multiple materials, or a reinforcing member such as a wire may be embedded therein.

The inside diameter of the outer sheath 31 can be selected as appropriate, and is, for example, 0.9 to 4.1 mm, more preferably 1.2 to 1.9 mm. The outside diameter of the outer sheath 31 can be selected as appropriate, and is, for example, 1.0 to 4.5 mm, more preferably 1.3 to 2.0 mm.

Constituent materials for the extension part 32 and the fixing part 33 preferably have sufficient strength, and for example, a shape memory alloy to which the shape memory effect and the super elasticity are assigned by thermal treatment, stainless steel, Ta, Ti, Pt, Au, W, polyolefin such as polyethylene or polypropylene, polyester such as polyamide or polyethylene terephthalate, fluorinated polymers such as ETFE, PEEK (polyether ether ketone), and polyimide, can be used suitably. As for the shape memory alloy, a Ni-Ti-based, Cu-Al-Ni-based, or Cu-Zn-Al-based alloy, any combination thereof, or the like is preferably used.

The length in the axis direction of the extension part 32 can be selected as appropriate, and is, for example, 0.3 to 50 mm, more preferably 1 to 5 mm. The thickness (length along the radial direction of the outer sheath 31) of the extension part 32 can be selected as appropriate, and is, for example, 0.05 to 1 mm. The width (length along the circumferential direction of the outer sheath 31) of the extension part 32 can be selected as appropriate, and is, for example, 0.1 to 2 mm.

A constituent material for the tip tube 34 is not specially limited, and for example, polyolefin such as polyethylene, polypropylene, ethylene-propylene copolymer, or ethylene-vinyl acetate copolymer, polyvinyl chloride, polystyrene, polyamide, or polyimide, or a combination thereof can be used suitably.

The inside diameter of the tip tube 34 can be selected as appropriate, and is, for example, 0.3 to 1.0 mm. The outside diameter of the tip tube 34 can be selected as appropriate, and is, for example, 0.4 to 1.4 mm. The length in the axis direction of the tip tube 34 can be selected as appropriate, and is, for example, 5 to 100 mm.

The cutting part 40 is a part for cutting a thrombus, and is fixed to the driving tube. In the illustrated embodiment, the cutting part 40 is hollow and fixed to the outer peripheral surface of the distal portion of the driving tube 21. The cutting part 40 is a cylinder that protrudes distally beyond the distal end of the driving tube 21. The distal side end portion of the cutting part 40 is provided with a ring-like sharp blade (cutting blade) 41 obtained by reducing an outside diameter of the cutting part 40 toward the distal side until the outside diameter coincides with an inside diameter of the cutting part 40.

A constituent material for the cutting part 40 preferably has sufficient strength to allow the cutting par 40 to cut a thrombus, and for example, stainless steel, Ta, Ti, Pt, Au, W, or a shape memory alloy can be used suitably. As for a constituent material for the cutting part 40, a resin including engineering plastic such as polyether ether ketone (PEEK) may be employed. The cutting part 40 may include a surface that is subjected to coating processing.

The inside diameter of the cutting part 40 preferably substantially coincides with the outside diameter of the driving tube 21 to be contacted, and is, for example, 0.8 to 40 mm. The outside diameter of the cutting part 40 preferably substantially coincides with the outside diameter of the outer sheath 31, and is, for example, 1.0 to 4.5 mm. The length in the axis direction of the cutting part 40 can be selected as appropriate, and is, for example, 0.5 to 4.0 mm.

The resistive body 50 is an elongated part that is disposed in the lumen of the driving shaft 20 so that relative rotation between the resistive body 50 and the driving shaft 20 occurs. As shown in FIG. 2, the outer surface of the resistive body 50 is spaced from the inner surface of the cutter to define a space through which the pieces of the object cut by the cutter 40 pass and enter the lumen in the driving shaft 20 by way of the open distal end of the driving shaft 20. The resistive body 50 suppresses a thrombus having entered the interior or lumen of the driving shaft 20 from rotating with the driving shaft 20. The shape of a cross section that is perpendicular to at least a part of the central axis of the resistive body 50 is a non-true circle (other than a perfect circle). The resistive body 50 is provided with a first resistive body (first resistive body part) 51 that is located on a distal side of the resistive body 50, and a second resistive body (second resistive body part) 52 that is unitary with and located on the proximal side of the resistive body 50. The first resistive body 51 and the second resistive body 52 respectively have cross sections of different shapes that are perpendicular to the central axis. The shape of the cross section perpendicular to the central axis of the first resistive body 51 is a perfect circle, and the shape of the cross section perpendicular to the central axis of the second resistive body 52 is an approximate rectangle. The resistive body 50 with such a configuration can be easily manufactured in such a manner that a part of a wire having a cross-sectional shape of a perfect circle remains without any change to obtain the first resistive body 51, and the other part(s) is crushed by being sandwiched between dies to obtain the flat plate-shaped second resistive body 52. The flat plate-shape means a shape that is relatively longer in one direction and relatively shorter in another direction orthogonal to the one direction, and has two surfaces generally facing opposite directions. The first resistive body 51 and the second resistive body 52 may be manufactured by joining different members. A distal side end portion of the resistive body 50 is fixed to the fixing part 33 closer to the distal side than the cutting part 40. The first resistive body 51 having a cross section of a perfect circular shape that is perpendicular to the central axis in a distal portion of the resistive body 50 is provided, so that an outer surface of the first resistive body 51 has a small resistance, and the thrombus can easily enter the cutting part 40 and the interior of the driving shaft 20. An interlock portion between the first resistive body 51 and the second resistive body 52 is located in an interior of the carrier 22. Accordingly, a thrombus can be guided to the interior of the carrier 22 along the first resistive body 51 having the outer surface with a small resistance. An end portion on a proximal side of the second resistive body 52 is located closer to the proximal side than the carrier 22. This allows the second resistive body 52 to suppress a thrombus together with the driving shaft 20 from rotating to the end portion on the proximal side of the carrier 22, and to maintain a high conveyance force. The end portion on the proximal side of the carrier 22 is located in the interior of the aspiration pipe body 70, but may not be located in the interior of the aspiration pipe body 70. An end portion on the proximal side of the resistive body 50 may be located closer to the proximal side than the first carrier 26, and closer to the distal side than the proximal side end portion of the second carrier 27. This can maintain a high conveyance force at a position of the first carrier 26 on the distal side where a high conveyance force is required.

The shape of the cross section perpendicular to the central axis of the second resistive body 52 is a non-true circle, so that a second space is located between the outer surface of the second resistive body 52 and an inner peripheral surface of the driving shaft 20 that relatively rotates. Moreover, a first space is defined between the first resistive body 51 and the inner peripheral surface of the driving shaft 20, and with an inner peripheral surface of the cutting part 40. The space between the resistive body 50 and the driving shaft 20 and the space between the resistive body 50 and the cutting part 40 effectively act in order to cause an aspiration force from the proximal side to act. Moreover, the first space and the second space have different shapes. The first space in a cross section perpendicular to the central axis of the medical device 10 has a ring-like shape (annular) having a width in the radial direction and an outer circumference and an inner circumference that are respectively concentric circles and perfect circles. The second space in a cross section perpendicular to the central axis of the medical device 10 has a ring-like shape (annular) having a width in the radial direction, and an outer circumference that is a circle partially recessed to an inner side in the radial direction and an inner circumference that is a rectangle.

The first resistive body 51 has cross sections of the same shape that are perpendicular to the central axis within the entire range in the axis direction. That is, the cross-section of the first resistive body 51 is the same along the entire length of the first resistive body 51. Accordingly, the first resistive body 51 has a surface, which is smooth along the axial direction. Thrombus and the like can thus smoothly slide t along the first resistive body 51. The second resistive body 52 has cross sections of the same shape that are perpendicular to the central axis within the entire range in the axial direction. Accordingly, the second resistive body 52 has a surface, which is smooth along the axial direction. Thrombus and the like can thus smoothly slide along the second resistive body 52.

A constituent material for the resistive body 50 preferably has sufficient strength to suppress the rotation of a thrombus, and for example, stainless steel, Ta, Ti, Pt, Au, W, or a shape memory alloy such as Nitinol (registered trademark) can be used suitably.

The operation unit 60 is a part that is gripped and operated by an operator. The operation unit 60 is provided with, as illustrated in FIG. 3, a casing 62 that includes the accommodation space 61 in an interior of the casing 62, a first seal part 63 that comes into contact with an outer peripheral surface of the driving shaft 20, and a second seal part 64 that comes into contact with an outer peripheral surface of the connection shaft 23.

The casing 62 is provided with a distal side through-hole 65 through which the driving tube 21 penetrates, a proximal side through-hole 66 through which the connection shaft 23 penetrates, and an aspiration hole 67 into which the syringe 100 can be interlocked. A proximal side opening portion 73 of the aspiration pipe body 70 is located in the accommodation space 61 in the interior of the casing 62. The aspiration pipe body 70 is a pipe body for guiding a negative pressure acted from the syringe 100 to a prescribed position in the interior of the driving tube 21. A distal side opening portion 72 of the aspiration pipe body 70 is located on the proximal side of the second carrier 27 in the interior of the driving tube 21. Accordingly, the syringe 100 is aspirated or operated to allow a negative pressure to be applied to the interior of the driving tube 21 via the aspiration pipe body 70.

The rotary drive unit 90 is provided with a drive source 91, such as a motor, as illustrated in FIG. 1, and is a part for the rotating driving shaft 20. The rotary drive unit 90 is provided with a rotatable rotation axis 92 to which the connection shaft 23 is connected. The rotary drive unit 90 is an external device that can be interlocked with and detached from the operation unit 60 in the present embodiment, but may be fixed to the operation unit 60. The rotary drive unit 90 is further provided with a switch, a battery, and the like, which are not illustrated.

Figure 11:
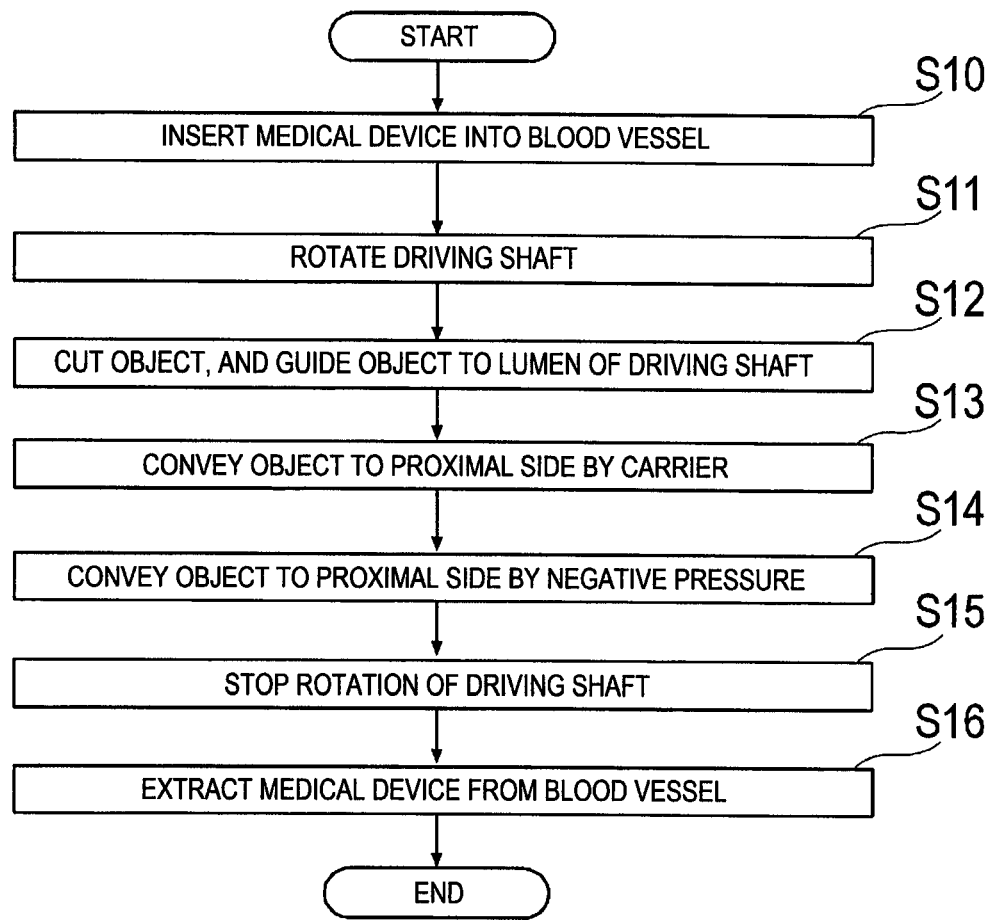
FIG. 11 is a flowchart for explaining a method using the medical device.

Next, a usage method of the medical device 10 according to the first embodiment will be described using a case where an intravascular thrombus, a calcified lesion, and the like are destroyed and aspirated (suctioned) as an example while referring to the flowchart in FIG. 11.

Firstly, the medical device 10 in which the rotary drive unit 90 is interlocked with the operation unit 60, and the connection shaft 23 is interlocked with the rotation axis 92, is prepared (see FIG. 1). In the medical device 10, the rotary drive unit 90 is operated to make the driving shaft 20 be in a rotatable state. That is, the rotary drive unit 90 is operated to rotate the driving shaft 20. Next, a proximal side end portion of a guide wire 110 is inserted into the guide wire lumen 35 of the medical device 10. Thereafter, the medical device 10 is inserted into a blood vessel and is advanced in the blood vessel to reach a proximal side of the thrombus T using the guide wire 110 as a guide (Step S10). That is, using the guide wire 10 as a guide, the medical device is inserted into and moved forward along the blood vessel to position the medical device on the proximal side or near side of the thrombus T.

Figure 9:
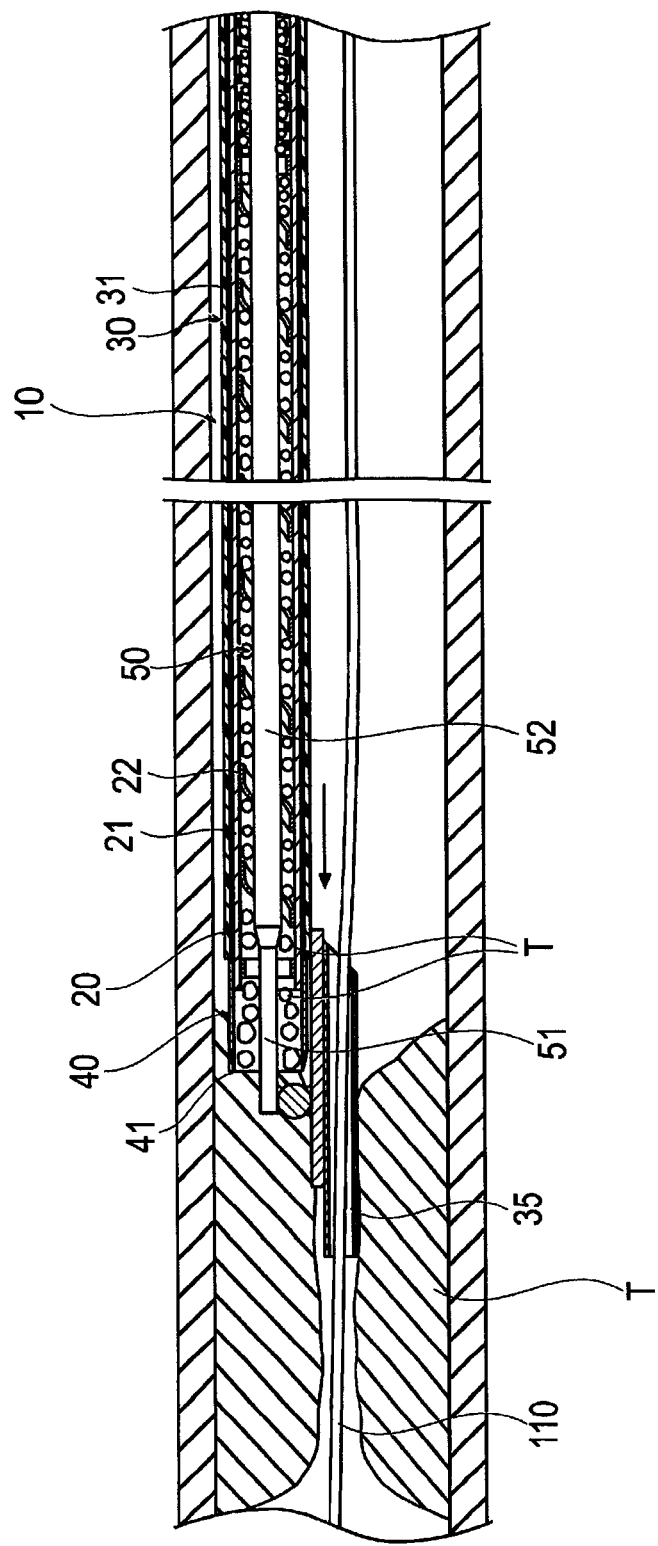
FIG. 9 is a cross-sectional view illustrating a state where the medical device removes a thrombus in the blood vessel.
Figure 10:
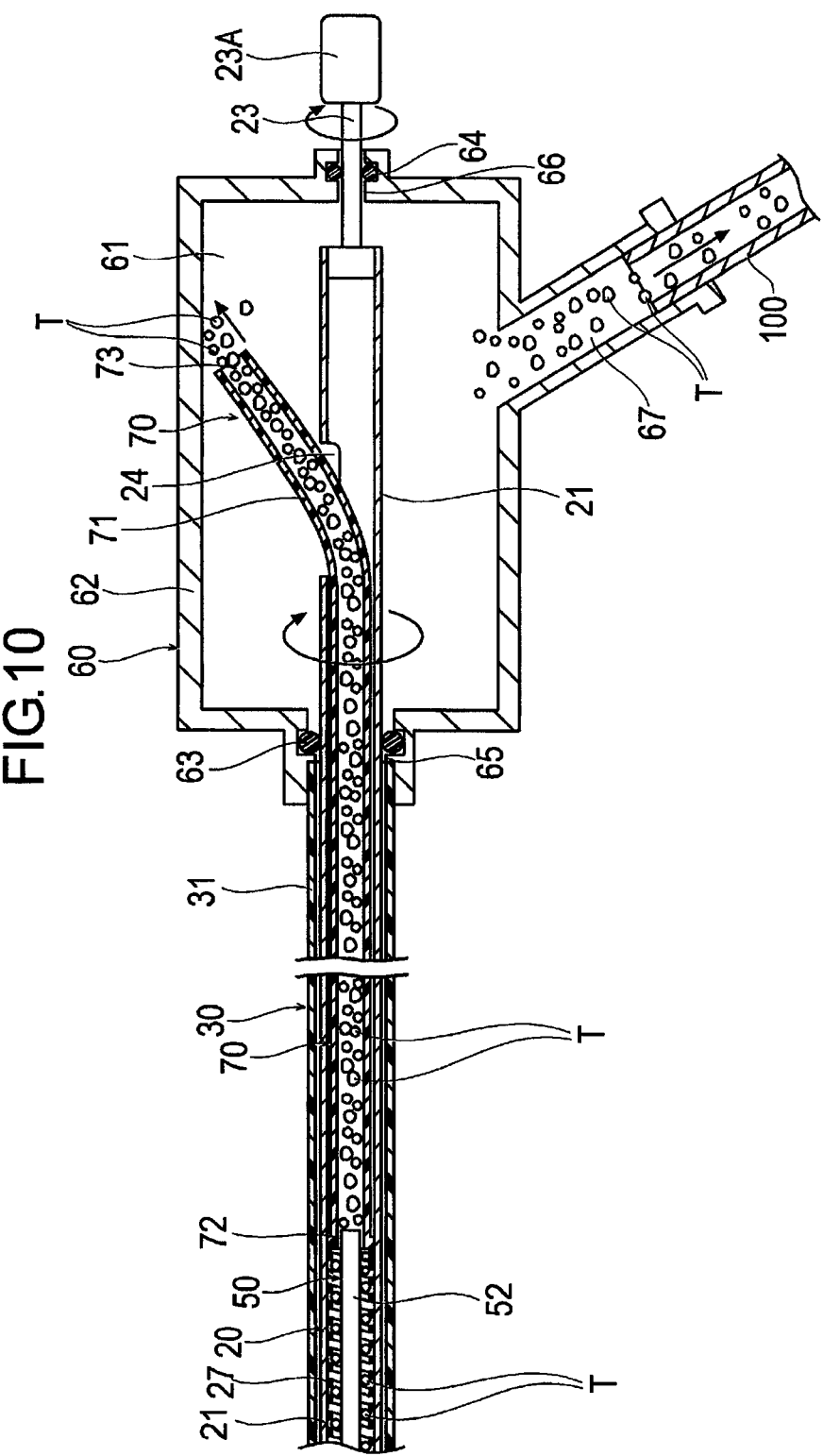
FIG. 10 is a cross-sectional view illustrating the proximal portion of the medical device when removing an intravascular thrombus.

Next, the rotary drive unit 90 is operated to rotate the driving shaft 20 (Step S11). Thereafter, the medical device 10 is moved in the forward direction (i.e., toward the thrombus T). As illustrated in FIGS. 9 and 10, this causes the blade 41 of the cutting part 40 to come into contact with the thrombus T, and the thrombus T is cut into cut thrombus pieces by the rotating cutting blade 41 (Step S12). The cut thrombus T enters the interior of the driving tube 21 through a lumen of the tubular cutting part 40. In this process, in the interior of the cutting part 40 is located the first resistive body 51 having a cross section of a perfect circular shape in a plane perpendicular to the central axis. Accordingly, the thrombus T is smoothly guided to the driving tube 21 along the outer surface with a small resistance of the first resistive body 51. It is also possible to make the cut thrombus T more easily enter the interior of the driving tube 21 through the lumen of the tubular cutting part 40 by pushing the medical device 10 in.

The thrombus T guided by the driving tube 21 comes into contact with the rotating first carrier 26. This causes the thrombus T to receive a force directing the thrombus T toward a proximal direction and a force directing the thrombus T toward a rotational direction, from the first carrier 26. In this process, the thrombus T is suppressed from rotating together with the first carrier 26 by the second resistive body 52 that penetrates through an interior of the first carrier 26 and does not rotate. Accordingly, the thrombus T linearly moves with high efficiency along the second resistive body 52 to the proximal side or in the proximal direction, by the force received from the rotating first carrier 26 and the reaction force received from the second resistive body 52. This allows the thrombus T to be conveyed to the proximal side by the first carrier 26 (Step S13). Moreover, the first carrier 26 having an inter-pitch distance longer than that of the second carrier 27 has a large amount of conveyance by one rotation. Accordingly, it is possible to maintain the lumens of the cutting part 40 and the driving shaft 20 on an inlet side into which the thrombus T enters in a state where the thrombus T does not clog the lumens.

When a plunger of the syringe 100 interlocked with the aspiration hole 67 is pulled, the accommodation space 61 of the operation unit 60 becomes in a negative pressure, and the interior of the aspiration pipe body 70 becomes in a negative pressure via the proximal side opening portion 73 of the aspiration pipe body 70. As a source for generating the negative pressure, the syringe 100 can be used, but the operation unit 60 can be also connected to an aspiration pump and the like.

When the interior of the aspiration pipe body 70 becomes in the negative pressure, the interior of the driving tube 21 communicated with the aspiration pipe body 70 is also under negative pressure. In this process, the aspiration pipe body 70 is disposed in an interior of the proximal portion of the driving tube 21. Accordingly, it is possible to suppress the negative pressure from escaping from the slit that is a gap between the wires forming the driving tube 21. In a region on the distal side from the aspiration pipe body 70, the carrier 22 can convey the thrombus, so that no aspiration pipe body 70 is provided and the slight escape of the negative pressure causes no problem. This can cause the negative pressure to excellently act in the range where the carrier 22 of the driving tube 21 is provided. When the negative pressure acts on the interior of the driving tube 21, the thrombus T in the interior of the driving tube 21 moves in the proximal direction to the proximal side. In this manner, the negative pressure is caused to act on the interior of the driving tube 21 to allow the thrombus T to be conveyed to the proximal side (Step S14). In this process, the rotating driving shaft 20 is located outward of a space serving as a conveyance path. Moreover, the resistive body 50 that is located inward of the rotating carrier 22 has a cross section of a non-true circular shape that is perpendicular to the central axis, so that a space is formed between an inner peripheral surface of the carrier 22 and the resistive body 50. Accordingly, it is possible to cause an aspiration force in the interior of the driving tube 21 that is generated due to the negative pressure to effectively act on the thrombus T. In this manner, the thrombus T linearly moves in the proximal direction toward the proximal side and is effectively conveyed, by both of the force by the first carrier 26 and the aspiration force. Note that, the aspiration by the syringe 100 may not be performed. Moreover, the first carrier 26 is partially fixed to the driving tube 21 and is deformable, so that the first carrier 26 can be deformed even in a case where the thrombus T is large, for example, which suppresses possible breakage and obtains high safety. Moreover, the first carrier 26 can be returned to an original shape after having been deformed when the first carrier 26 includes an elastically deformable material, such as a shape memory alloy, and thus can maintain the performance thereof.

The thrombus T having moved in the proximal direction closer to the proximal side than the first carrier 26 reaches a position at which the second carrier 27 in the interior of the driving tube 21 is provided. This causes the thrombus T to receive a force to direct the thrombus T toward the proximal direction and a force to direct the thrombus T toward the rotation direction, from the second carrier 27. In this process, the thrombus T is suppressed from rotating together with the second carrier 27 by the second resistive body 52 that is positioned in or penetrates through the interior of the second carrier 27 and does not rotate. Accordingly, the thrombus T linearly moves with high efficiency along the second resistive body 52 in the proximal direction to the proximal side, by the force received from the rotating second carrier 27 and the reaction force received from the second resistive body 52.

Moreover, the thrombus T having reached a position at which the second carrier 27 in the interior of the driving tube 21 is provided receives an aspiration force from the aspiration pipe body 70, similar to the case where having reached at the position where the first carrier 26 is provided. This also causes the thrombus T to linearly move toward the proximal side, so that the thrombus T is effectively conveyed by both of the force by the second carrier 27 and the aspiration force. The aspiration by the syringe 100 may not be performed. Moreover, the second carrier 27 is partially fixed to the driving tube 21 and is deformable, so that the second carrier 27 can be deformed even in a case where the thrombus T is large, for example, which suppresses possible breakage and obtains high safety. Moreover, the second carrier 27 can be returned to an original shape after having been deformed when the second carrier 27 includes an elastically deformable material, such as a shape memory alloy, and thus can maintain the performance thereof. Further, the resistive body 50 is located closer to the proximal side than the first carrier 26 and the second carrier 27 (i.e., the resistive body 50 extends throughout the entire length of the both the first carrier 26 and the second carrier 27), so that the conveyance by the first carrier 26 and the second carrier 27 is excellently performed.

The thrombus T having reached closer to the proximal side than the second carrier 27 is aspirated in the interior of the aspiration pipe body 70 (drawn into the interior of the aspiration pipe body 70 by suction), and moves to the proximal side in the interior of the aspiration pipe body 70. Thereafter, the thrombus T in the interior of the aspiration pipe body 70 is discharged into the interior of the syringe 100 via the accommodation space 61.

Moreover, a cross-sectional area of the gap between the outer sheath 31 and the driving tube 21 is sufficiently smaller than a cross-sectional area of the interior of the aspiration pipe body 70, so that it is possible to suppress an aspiration force that acts on the interior of the driving tube 21 from the aspiration pipe body 70 from escaping into a space between the outer sheath 31 and the driving tube 21.

Moreover, when the syringe 100 causes the negative pressure to be generated in the accommodation space 61, the accommodation space 61 is sealed by the first seal part 63 and the second seal part 64, so that it is possible to cause the negative pressure to effectively act on the interior of the driving tube 21.

Further, the thrombus T is cut by moving the cutting part 40 while the cutting part 40 is being reciprocated in the axis direction, and is continuously conveyed and aspirated (suctioned), so that it is possible to rapidly remove the thrombus T. In this process, an aspiration force acts on the inlet of the cutting part 40, so that it is possible to aspirate the cut thrombus T without the thrombus T escaping as much as possible.

After the cutting, the conveyance, and the aspiration (suction) of the thrombus T have been completed, the rotation movement of the driving shaft 20 is stopped (Step S15). Next, the medical device 10 is extracted from the blood vessel, and the treatment is completed (Step S16).

As in the foregoing, the medical device 10 according to the first embodiment is the medical device 10 for removing the thrombus T (object) in the blood vessel (body lumen), and includes the rotatable tubular driving shaft 20 in which the spiral-shaped carrier 22 is provided on an inner surface of the driving shaft 20, the cutting part 40 that is provided on the distal side of the driving shaft 20, rotates together with the driving shaft 20, and cuts the thrombus T, and the elongated resistive body 50 that is disposed in the lumen of the driving shaft 20 and can be rotated relative to the driving shaft 20. The medical device 10 configured as above can smoothly guide the thrombus T cut by the rotating cutting part 40 to the lumen of the driving shaft 20 that rotates together with the cutting part 40. In this process, a force is caused to act on the thrombus T by the carrier 22 that is provided at an inner peripheral surface of the driving shaft 20 while suppressing the rotation of the thrombus T by the resistive body 50, so that it is possible to move the thrombus T in a desired direction along the resistive body 50. Accordingly, it is possible to cut and effectively remove the intravascular thrombus T.

Moreover, the cutting part 40 has a cylindrical shape, and has a sharp edge at an opening portion (open end) that is located on the distal side or distal end of the cutting part 40. The medical device 10 is moved to the distal side and the cutting part 40 contacts the thrombus T. Further, as the medical device 10 is kept moving toward the distal side after the cutting part 40 contacts the thrombus T, the thrombus T comes into or enters the inside of the cutting part 40. Accordingly, it is possible to rapidly cut the thrombus T by the first cutting part 40, and convey the thrombus T with high efficiency by the carrier 22.

Moreover, the medical device 10 includes the outer sheath 31 that rotatably contains the driving shaft 20, and the resistive body 50 is directly or indirectly fixed to the outer sheath 31. This can excellently maintain the relative rotation of the driving shaft 20 to which the cutting part 40 is fixed and the resistive body 50, and can maintain the excellent cutting by the cutting part 40.

Moreover, also disclosed is a treatment method of removing the thrombus T (object) of a lesion area in the blood vessel (body lumen) using the aforementioned medical device 10. The treatment method includes: inserting the medical device 10 into a blood vessel (Step S10); cutting the intravascular thrombus T by rotating the cutting part 40 by the driving shaft 20, and guiding the cut thrombus T to the lumen of the driving shaft 20 (Step S12); conveying the thrombus T to the proximal side by acting a force on the thrombus T by the carrier 22 that is provided in the rotating driving shaft 20 while suppressing the rotation of the thrombus T by the resistive body 50 (Step S13); and extracting the medical device 10 from the interior of the blood vessel (Step S16). The treatment method configured as the above can cut the thrombus T by the rotation of the cutting part 40, and smoothly guide the thrombus T to the lumen of the driving shaft 20 that rotates together with the cutting part 40. In this process, a force is caused to act on the thrombus T by the carrier 22 that is provided to an inner peripheral surface of the driving shaft 20 while suppressing the rotation of the thrombus T by the resistive body 50, so that it is possible to convey the thrombus T into a desired direction along the resistive body 50. Accordingly, it is possible to cut and effectively remove the intravascular thrombus T.

Second Embodiment

A medical device according to a second embodiment differs from the medical device 10 according to the first embodiment only in that a second cutting part 210 is provided. In the description below, features that are the same or similar to those described above are identified by the same reference numerals and a detailed description of such features is not repeated.

Figure 12:
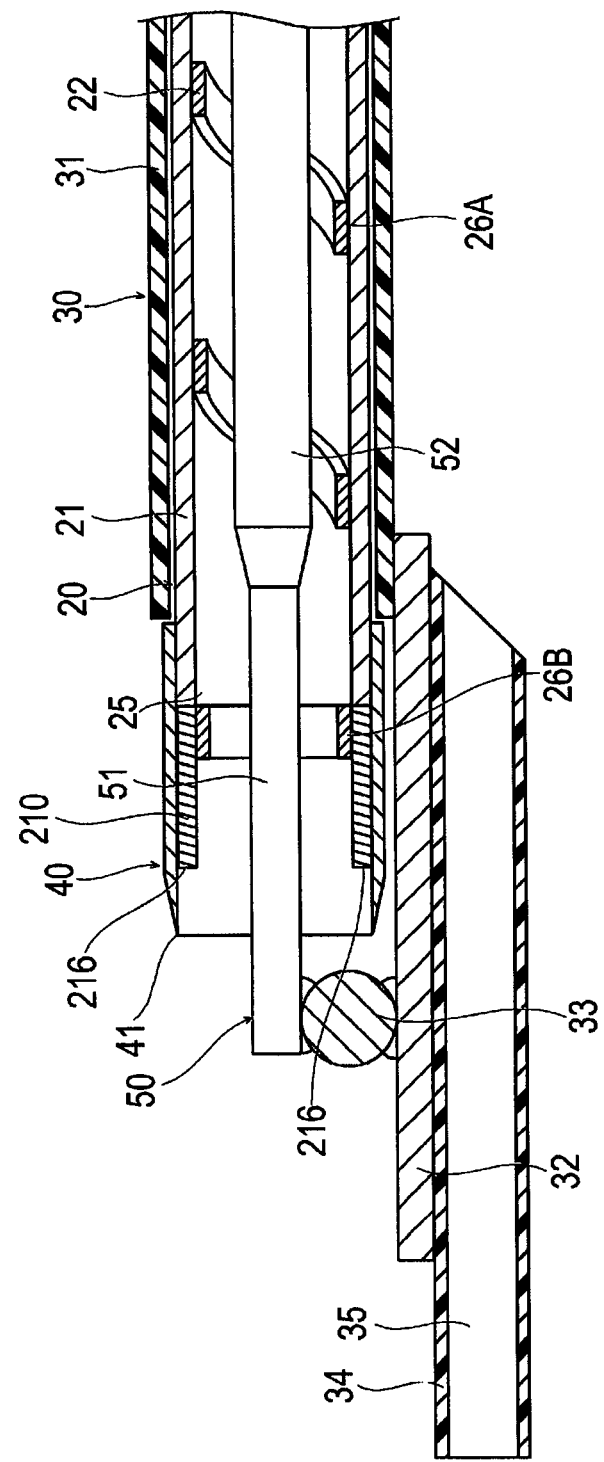
FIG. 12 is a cross-sectional view illustrating a distal portion of a medical device according to a second embodiment.
Figure 13:
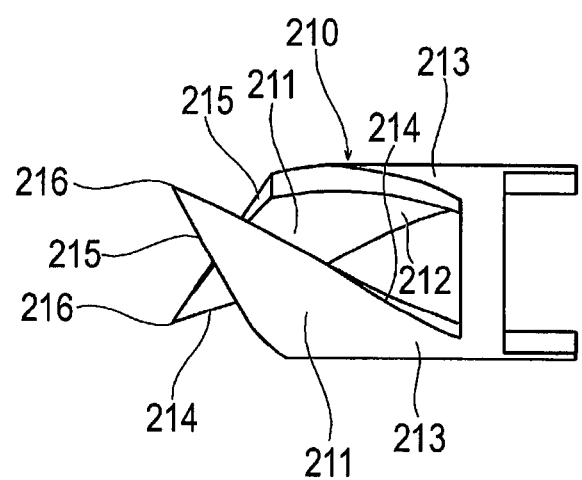
FIG. 13 is a plan view illustrating a second cutting part of the medical device according to the second embodiment.

The second cutting part 210 is fixed to the outer peripheral surface of the distal side ring part 26B of the first carrier 26, as illustrated in FIGS. 12 and 13. The second cutting part 210 includes two spiral-shaped sharp cutting blades 211. The two cutting blades 211 have rotationally symmetrical shapes with respect to the central axis of the first carrier 26. Each cutting blade 211 includes a concave-like inner surface 212 that heads toward the central axis of the first carrier 26, and a convex-like outer surface 213 that is an opposite surface of the inner surface 212, and includes a first end face 214 and a second end face 215 between the inner surface 212 and the outer surface 213. The first end face 214 is a surface that directs to the proximal side, and is inclined at the same angle as (or different angle from) the spiral of the first carrier 26. The second end face 215 is a surface that directs to the distal side, and is inclined with respect to the central axis of the first carrier 26 at an angle that is larger than that of the spiral of the first end faces 214 and an angle equal to or less than 90 degrees. The first end faces 214 and the second end face 215 intersect on the distal side to constitute a sharp second blade 216. The second cutting part 210 is disposed inward of the cutting part 40 (first cutting part). The outer surface 213 of the second cutting part 210 comes into contact with the inner peripheral surface of the cutting part 40. The second blade 216 that is located on the most distal side of the second cutting part 210 is located closer to the proximal side than the blade 41 of the cutting part 40. Accordingly, the second cutting part 210 can finely destroy the thrombus T having been cut by the first cutting part, and guide it to the interior of the driving tube 21. Moreover, the second cutting part 210 can cut also the thrombus T before being cut by the cutting part 40.

The second blade 216 of the second cutting part 210 is inclined with respect to the central axis of the first carrier 26, so that the second blade 216 can cut into the thrombus T by rotation, and scrape-off the thrombus T. Accordingly, the second cutting part 210 is different from the cutting part 40 that acts so as to cut off the thrombus T by being pushed into the distal side. The cutting part 40 cuts off the thrombus T by being pushed down, so that the cutting part 40 can cut a large amount of comparatively soft thrombi T. In contrast, the second cutting part 210 scrapes-off the thrombus T by the rotation force, so that the second cutting part 210 can destroy the hard thrombus T. In this manner, the medical device is provided with both of the cutting part 40 and the second cutting part 210 to allow a variety of the thrombi T to be cut.

The first carrier 26 may include no distal side ring part 26B. In this case, the spiral-shaped spiral part 26A further extends to the distal side, and constitutes the distal side end portion of the first carrier 26. In this case, the distal side end portion of the spiral part 26A is disposed so as to follow an inner peripheral surface of the second cutting part 210. This can continuously guide the object cut by the second cutting part 210 to the spiral part 26A. Accordingly, the thrombus T is easily sent to the proximal side in the lumen of the driving shaft 20, and the lumen hardly clogs up.

Moreover, the second cutting part 210 is provided with the spiral-shaped first end faces 214, so that it is possible to smoothly guide the cut thrombus T to the first carrier 26. When an inclined angle of the first end faces 214 is identical with an inclined angle of the spiral of the first carrier 26, it is possible to guide the thrombus T more smoothly to the first carrier 26. The second cutting part 210 also functions as a carrier, so that the second cutting part 210 has an effect even when having no second blade 216 for cutting the thrombus T.

Moreover, the second cutting part 210 is located in a gap between an inner peripheral surface of the first carrier 26 and an inner peripheral surface of the cutting part 40. Accordingly, as compared with a case where no second cutting part 210 is provided, the thrombus T can smoothly enter the interior of the first carrier 26.

As in the foregoing, the medical device according to the second embodiment is a medical device 10 that can be used to remove a thrombus T (object) in the blood vessel (body lumen), and includes the rotatable tubular driving shaft 20, the cutting part 40 that is provided on the distal side of the driving shaft 20, rotates together with the driving shaft 20, and cuts the thrombus T, and the second cutting part 210 that is disposed near the distal side of the driving shaft 20, inward of the cutting part 40. The medical device configured as above can smoothly guide the thrombus T cut by the rotating cutting part 40 and the second cutting part 210 to the lumen of the driving shaft 20 that rotates together with the cutting part 40. In this process, the cutting part 40 and the second cutting part 210 having different characteristics can cut the thrombus T, so that it is possible to excellently cut and remove the various thrombi T having different characteristics, such as the material, the hardness, the viscosity, and the shape, by one device.

Moreover, the cutting part 40 has a sharp edge of an opening portion that is located on the distal side. The medical device 10 is moved to the distal side and the cutting part 40 contacts the thrombus T. Further, as the medical device 10 is kept moving toward the distal side after the cutting part 40 contacts the thrombus T, the thrombus T comes into or enters the inside of the cutting part 40. Accordingly, it is possible to rapidly cut the thrombus T by the first cutting part 40, and convey the thrombus T with high efficiency by the carrier 22.

Moreover, the second cutting part 210 includes the second blade 216 that cuts the thrombus toward the rotation direction by rotation. This causes the second cutting part 210 to cut the thrombus T by a rotation force, so that it is possible to generate a higher cutting force, as compared with a case where the thrombus T is cut only by the first cutting part 40 being pushed down. Accordingly, for example, it is possible to effectively cut even the hard thrombus T by the second cutting part 210.

Moreover, the second blade 216 is inclined with respect to the central axis of the second cutting part 210. This allows the second blade 216 to cut the thrombus T toward the rotation direction by rotation, and move the cut thrombus T in the proximal direction to the proximal side.

Moreover, the second blade 216 of the second cutting part 210 is located closer to the proximal side than the blade 41 of the first cutting part 40. That is, the second blade 216 of the second cutting part 210 is positioned proximal of the blade 41 of the first cutting part 40. This allows the thrombus T that can be cut by the first cutting part 40 being pushed down to be rapidly cut by the first cutting part 40, and the thrombus T that has been cut by the cutting part 40 to be cut more finely by the rotating second cutting part 210. Accordingly, it is possible to make the thrombus T easily enter the lumen of the driving shaft 20.

Moreover, the description also describes a treatment method of removing the thrombus T (object) of a lesion area in the blood vessel (body lumen) using the medical device according to the second embodiment. The treatment method includes: inserting a medical device into a blood vessel; cutting the intravascular thrombus T by rotating the cutting part 40 and the second cutting part 210 by the driving shaft 20, and guiding the cut thrombus T to the lumen of the driving shaft 20; conveying the thrombus T in the proximal direction to the proximal side by the rotating driving shaft 20; and extracting the medical device from the interior of the blood vessel. The treatment method configured as the above can cut the thrombus T by the cutting part 40 and the second cutting part 210 that are rotating, and smoothly guide the thrombus T to the lumen of the driving shaft 20 that rotates together with the cutting part 40 and the second cutting part 210. In this process, the cutting part 40 and the second cutting part 210 having different characteristics can cut the thrombus T, so that it is possible to excellently cut and remove the various thrombi T having different characteristics, such as the material, the hardness, the viscosity, and the shape, by one device.

Third Embodiment

A medical device according to a third embodiment is different from the medical device according to the second embodiment only in the structure of a resistive body 310. In the description below, features that are the same or similar to those in the first and second embodiments described above are identified by the same reference numerals and a detailed description of such features is not repeated.

Figure 14:
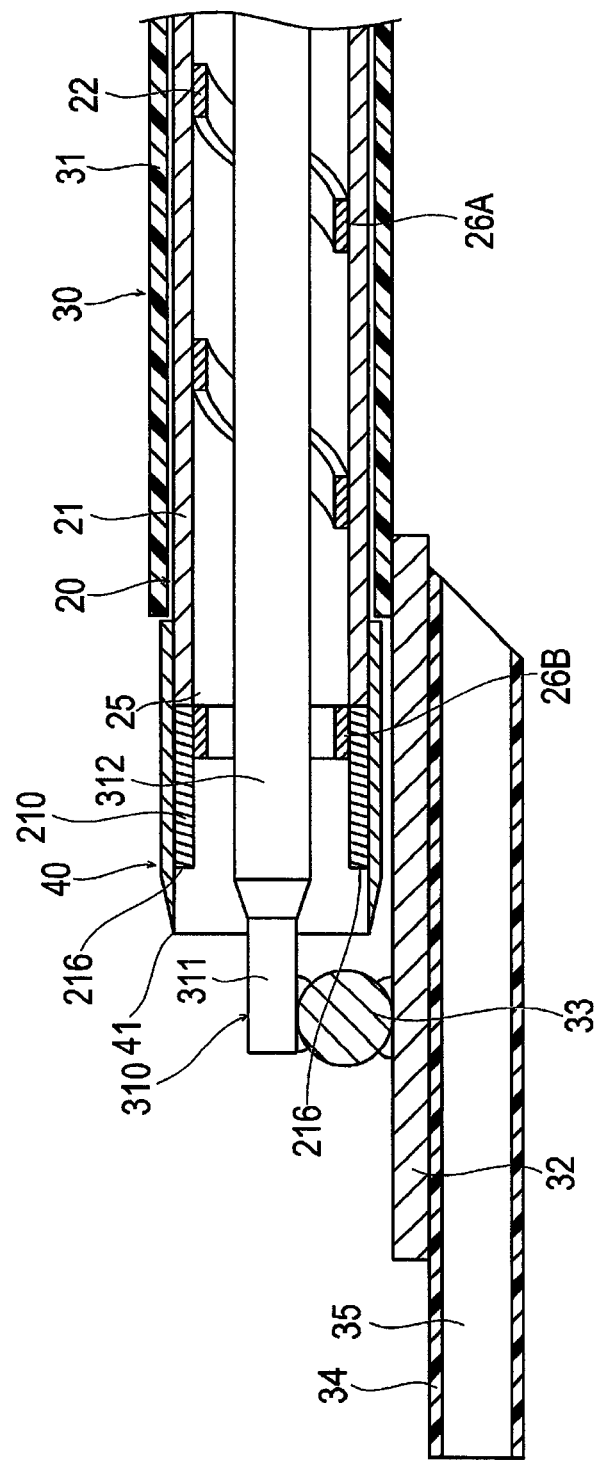
FIG. 14 is a cross-sectional view illustrating a distal portion of a medical device according to a third embodiment.

In the third embodiment, as illustrated in FIG. 14, a first resistive body 311 having a perfect circular shape of a cross section perpendicular to the central axis of the resistive body 310 is located closer to the distal side than the second cutting part 210. That is, the proximal end of the first resistive body 311 having the perfectly circular cross section, as seen in a plane perpendicular to the central axis of the resistive body 310, is positioned distal of the distal end of the second cutting part 210. In other words, a distal side end portion of a second resistive body 312 having a cross section of a non-circular shape perpendicular to the central axis is located closer to the proximal side than the blade 41 of the first cutting part 40 and closer to the distal side than the second blade 216 of the second cutting part 210. That is, the distal side end portion of the second resistive body 312 having a non-true circular cross sectional shape in a plane perpendicular to the central axis is located proximal of the distal end of the blade 41 of the first cutting part 40 and is located distal of the distal end of the second blade 216 of the second cutting part 210. Accordingly, the second resistive body 312 that suppresses the rotation of the thrombus T is located in the interior of the second cutting part 210. The second cutting part 210 cuts the thrombus T by the rotation force, so that the second cutting part 210 can excellently cut the thrombus T by the rotation of the thrombus T in the interior of the second cutting part 210 being suppressed. Moreover, the second cutting part 210 is also a carrier that is provided with the spiral-shaped first end faces 214, so that the second cutting part 210 can smoothly guide the thrombus T to the lumen of the driving tube 21 by the rotation of the thrombus T in the interior thereof being suppressed by the second resistive body 312.

Fourth Embodiment

A medical device according to a fourth embodiment differs from the medical device according to the third embodiment only in the axial length of a second cutting part 410. In the description below, features that are the same or similar to those in the first, second and third embodiments described above are identified by the same reference numerals and a detailed description of such features is not repeated.

Figure 15:
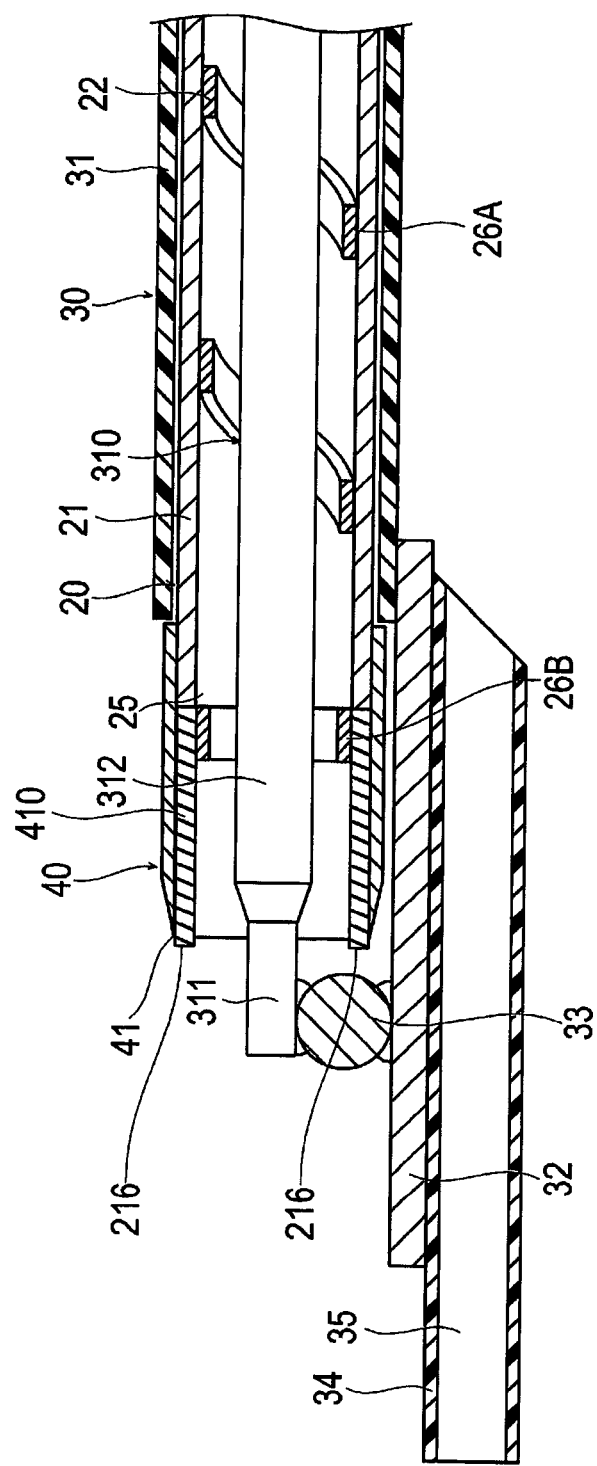
FIG. 15 is a cross-sectional view illustrating a distal portion of a medical device according to a fourth embodiment.

In the fourth embodiment, as illustrated in FIG. 15, the second blade 216 that is located on the most distal side of the second cutting part 410 is located closer to the distal side than the blade 41 of the cutting part 40. That is, the distal end (tip end) of the second blade 216 of the second cutting part 410 is positioned distal of the distal end (tip end) of the blade 41 of the cutting part 400. Accordingly, the second cutting part 410 can effectively cut the thrombus T before the cutting part 40 is used to cut the thrombus T. Accordingly, it is possible to effectively cut the hard thrombus T by the second cutting part 410 and to guide it into the interior of the driving tube 21. Therefore, the medical device according to the fourth embodiment is effective in cutting multiple hard thrombi T. The position of the second blade 216 of the second cutting part 410 may be the same in the axial direction as the position of the blade 41 of the cutting part 40. That is, the distal end of the second blade 216 of the second cutting part 410 and the distal end of the blade 41 of the cutting part 400 may be at the same axial position. In this case, the medical device can cause both of the first cutting part 40 and the second cutting part 410 to simultaneously act on the thrombus T to allow a variety of the thrombi T to be cut with a good balance.

In the fourth embodiment, the second blade 216 of the second cutting part 410 is located closer to the distal side than the blade 41 of the cutting part 40 (first cutting part) so that the tip end of the second blade 216 is positioned distally beyond the tip end of the blade 41. Accordingly, it is possible to cut the thrombus T by the rotating second cutting part 410 before the cutting part 40 is used for cutting. Accordingly, it is possible to effectively cut, by the second cutting part 410, the thrombus T that is difficult to be cut only by the cutting part 40 being pushed down. Accordingly, it is possible to cut with a good balance a variety of the thrombi T including a hard thrombus, for example.

Fifth Embodiment

A medical device according to a fifth embodiment is different from the medical device according to the fourth embodiment only in the shape of a second cutting part 510. In the description below, features that are the same or similar to those in the first to fourth embodiments described above are identified by the same reference numerals and a detailed description of such features is not repeated.

Figure 16:
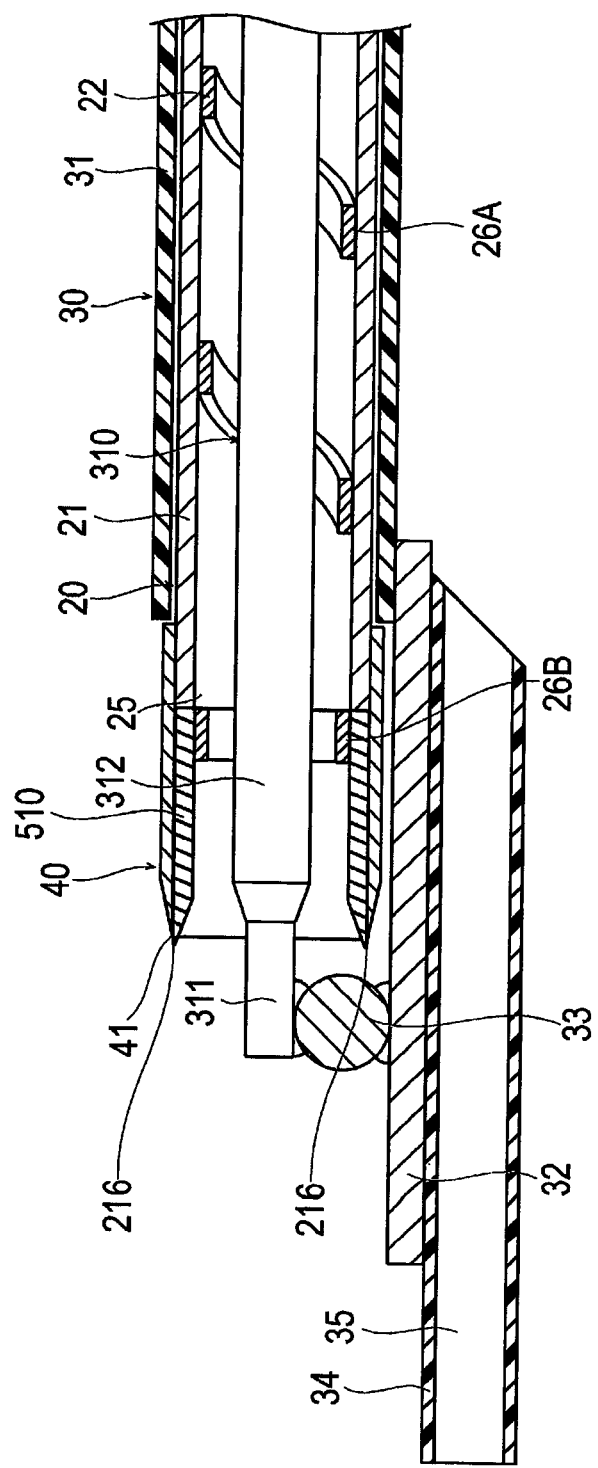
FIG. 16 is a cross-sectional view illustrating a distal portion of a medical device according to a fifth embodiment.

In the fifth embodiment, as illustrated in FIG. 16, an inside diameter of the second cutting part 510 becomes gradually larger in a tapered shape toward a blade at the distal end. In other words, the second blade 216 of the second cutting part 510 becomes thinner toward the distal side. Accordingly, a cutting force received by the thrombus T that enters the interior of the second cutting part 510 gradually becomes larger toward the distal side with respect to the second cutting part 510. Accordingly, it is possible to smoothly guide the thrombus T to the interiors of the second cutting part 510 and the cutting part 40 with low resistance.

Sixth Embodiment

A medical device according to a sixth embodiment is different from the medical device according to the second embodiment only in the structure of a first cutting part 810. In the description below, features that are the same or similar to those in the first to fifth embodiments described above are identified by the same reference numerals and a detailed description of such features is not repeated.

Figure 17:
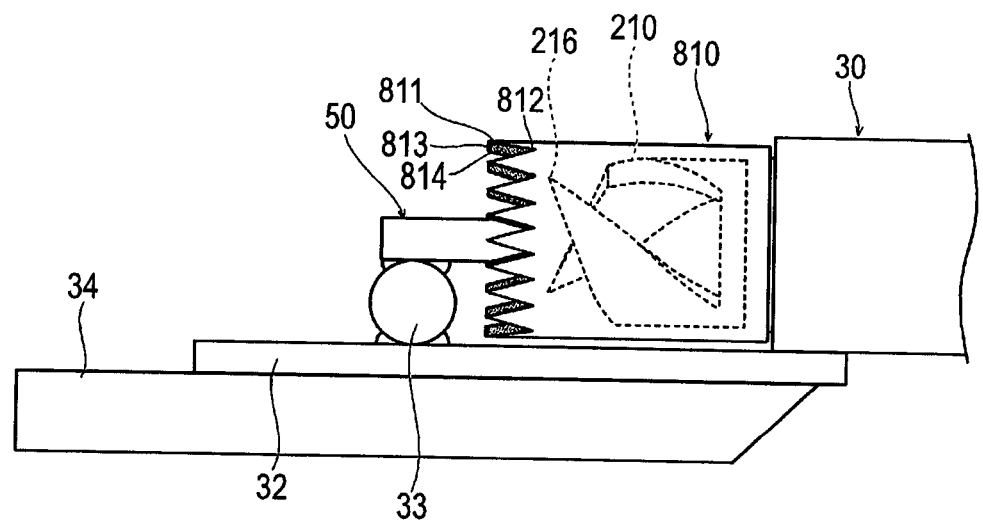
FIG. 17 is a plan view illustrating a distal portion of a medical device according to a sixth embodiment.

In the sixth embodiment, as illustrated in FIG. 17, a distal side end portion of the tubular first cutting part 810 is formed in a saw-tooth shape by sharp or pointed convex portions 811 and concave portions 812 being alternately arranged in the circumferential direction of the distal side end portion of the tubular first cutting part 810. The convex portions 811 may each be provided as a sharp blade 813 in an end portion that is tapered toward the distal side or distal end. Moreover, the surface of the convex portions 811 may be provided with surface-roughening grinding particles 814 for imparting grinding capabilities to the convex portions 811. As an alternative, grinding particles need not be provided on the surfaces of the convex portions 811. The second cutting part 210 is disposed in the interior of the first cutting part 810. The blades 813 are located closer to the distal side than the second blades 216 of the second cutting part 210 (i.e., the tip ends of the blades 813 are positioned distally beyond the second blades 216 of the second cutting part 210), but the position is not limited thereto. In the illustrated embodiment, the distal ends of the second blades 216 of the second cutting part 210 are proximal of the proximal end of the concave portions 812 as shown in FIG. 17.

In the treatment using the medical device according to the sixth embodiment, when a stenosed site such as the thrombus T is formed of comparatively hard tissues, it is possible to efficiently cut the stenosed site due to the rotation of the first cutting part 810, by the blades 813 and the grinding particles 814 of the first cutting part 810 contacting and cutting the thrombus T. In contrast, when the stenosed site is formed of the comparatively soft tissues, it is possible to effectively cut the stenosed site by pushing down the first cutting part 810 into the stenosed site due to the movement of the first cutting part 810 in the axial direction. That is, the first cutting part 810 can be moved or pushed into contact with the stenosed site. In addition, when this medical device is used to treat a mixed lesion in which the stenosed site includes both of a hard tissue and a soft tissue, this medical device can simultaneously conduct cutting by the blades 813 and the grinding particles 814, and cutting with the movement of the first cutting part 810 in the axis direction. Accordingly, this medical device can effectively cut the stenosed site. The mixed lesion that has been cut by the first cutting part 810 is further finely cut by the rotating second cutting part 20, and is effectively conveyed to the proximal side by the second cutting part 210. The second cutting part 20 is disposed in the interior of the cylindrically-shaped first cutting part 810. The number of blades in the first cutting part 81 is more than the number of blades in the second cutting part 20. This makes it easy to secure the lumen of the driving shaft 20, thereby allowing easy aspiration.

When the hard tissue is cut by the first cutting part 810, a powdered cutting fragment may be generated in some cases. In this process, the second cutting part 20 is rotated to generate a flow (fluid flow) in the proximal direction to make it easy to aspirate or move/suction the powdered cutting fragments in the proximal direction.

Figure 18:
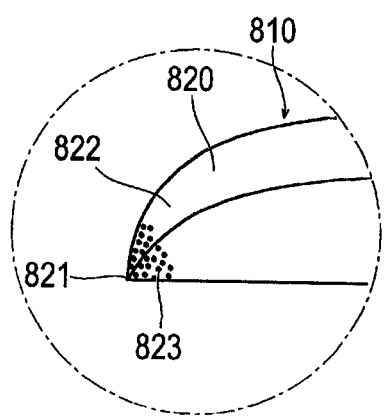
FIG. 18 is a perspective view illustrating a modification example of a convex portion of the medical device according to the sixth embodiment.

A convex portion 820 according to a modification example of the cylindrically-shaped first cutting part 810 may include, as illustrated in FIG. 18, a smooth outer surface part 822 formed outward (radially outward) of a distal end blade 821 of the convex portion 820. Grinding particles 823 are provided in the vicinity of the blade 821 on a distal end of the convex portion 820. According to an alternative, no grinding particles 823 may be provided. The outer surface part 822 is located radially outward of the blade 821 of the first cutting part 810. The outer surface part 822 is subjected to Rounding processing, for example, and is formed as a curved surface that is curved in a convex shape. Accordingly, even when the blade 821 comes into contact with a blood vessel wall, a vascular wall, or a guiding sheath, the outer surface part 822 can smoothly slide on the blood vessel wall, the vascular wall, or the guiding sheath. Accordingly, it is possible to preferably suppress the blood vessel wall, the vascular wall, or the guiding sheath from being damaged.

The invention is not limited to the above-described embodiments, but various changes by those skilled in the art can be made within the technical scope of the present invention. For example, the body lumen into which the medical device is inserted is not limited to the blood vessel, but may be the vessel, the ureter, the bilary duct, the oviduct, or the hepatic duct, for example. Accordingly, the object to be destroyed may be an object other than the thrombus.

Figure 19:
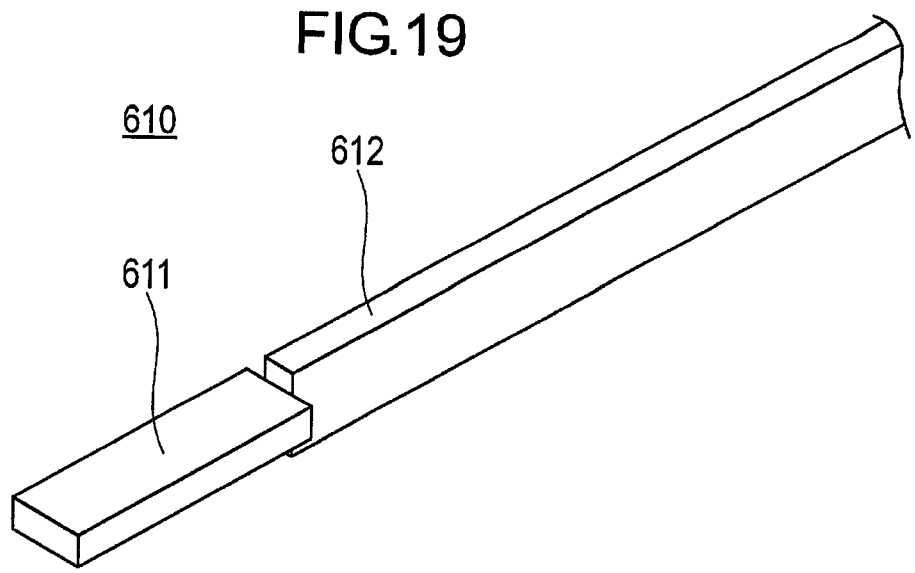
FIG. 19 is a perspective view illustrating a modification example of a resistive body

Moreover, the resistive body may not include a part having a cross section of a perfect circular shape perpendicular to the central axis. For example, as in a modification example illustrated in FIG. 19, both a first resistive body 611 and a second resistive body 612 in a resistive body 610 respectively have cross sections of rectangular shapes perpendicular to the central axis, and elongated axes of the respective cross sections may be orthogonal to each other.

Figure 20:
FIG. 20 is a cross-sectional view illustrating another modification example of the resistive body.

Moreover, in another modification example illustrated in FIG. 20, a resistive body 710 may be twisted. The rotation direction of the torsion may be the same as or different from the rotation direction of the spiral of the carrier. The inter-pitch distance of the torsion is preferably longer than the inter-pitch distance of the carrier. This allows the thrombus T that receives the rotation force from the carrier to be conveyed in the axis direction while the thrombus T is released to some extent in the rotation direction along the resistive body 710. Accordingly, it is possible to transmit the force to the thrombus T with high efficiency, and covey the thrombus T with an optimal route.

Moreover, although the carrier 22 in the above-described embodiments includes both of the first carrier 26 and the second carrier 27, the carrier 22 may include either one. Moreover, the carrier may further include one or more other carriers different from the first carrier 26 and the second carrier 27.

Moreover, the shape of a cross section perpendicular to the central axis of the resistive body is not specially limited as long as it is a non-true circle, and may be an elliptical shape, a triangle shape, or a quadrilateral or polygonal shape, for example.

The detailed description above describes embodiments of a medical device and method representing examples of the inventive medical device and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for removing an object in a body lumen, the medical device comprising:
    a rotatable tubular driving shaft positionable in the body lumen, the rotatable tubular driving shaft possessing a distal portion at a distal end of the rotatable tubular driving shaft;
    a cylindrically-shaped first cutter configured to cut the object, the cylindrically-shaped first cutter being provided on the distal portion of the driving shaft so that the cylindrically-shaped first cutter rotates together with the driving shaft; and
    a carrier connected to the rotatable tubular driving shaft so that the carrier rotates together with the rotatable tubular driving shaft, the carrier being positioned inside the rotatable tubular driving shaft, the carrier including a distal end at which is located a spiral-shaped surface that rotates with the carrier and is configured to cut the object.

2. The device according to claim 1, wherein the cylindrically-shaped first cutter possesses a distal end portion at which is located an open distal end of the first cutter, the first cutter including an axially extending tapered sharp edge at the open distal end of the first cutter.

3. The device according to claim 1, wherein the first cutter possesses an axially extending distal end portion, the distal end portion of the first cutter including pointed convex portions and concave portions that alternate with one another in a circumferential direction of the first cutter.

4. The device according to claim 3, wherein each of the pointed convex portions possesses a radially outwardly facing outer surface part that is curved in a convex shape.

5. The medical device according to claim 1, wherein the spiral-shaped surface is a part of a rotatable second cutting part that includes a second blade that cuts the object toward a rotation direction by rotation of the second cutting part.

6. The medical device according to claim 5, wherein the second blade is inclined with respect to the central axis of the second cutting part.

7. The medical device according to claim 5, wherein the second blade possesses an inside diameter, the inside diameter of the second blade gradually increasing in a tapering shape toward a distal end of the second blade.

8. The medical device according to claim 5, wherein the first cutter includes a sharp first blade possessing a tip end, the second blade of the second cutting part including a tip end positioned distally beyond the tip end of the first blade of the first cutter.

9. The medical device according to claim 5, wherein the cylindrically-shaped first cutter extends in an axial direction, the first cutter including a sharp first blade possessing a tip end and the second being a sharp second blade possessing a tip end, the tip end of the first blade and the tip end of the second blade being positioned relative to one another in the axial direction such that: i) the tip end of the first blade and the tip end of the second blade are axially aligned; or ii) the tip end of the second blade is positioned proximal of the tip end of the first blade.

10. The medical device according to claim 1, wherein the distal end of the carrier at which is located the spiral-shaped surface is sharp.

11. The medical device according to claim 1, wherein a sharp cutting blade is provided at the distal end of the carrier, the spiral-shaped surface being a part of the sharp cutting blade.

12. A medical device for removing an object in a body lumen, the medical device comprising:
    a rotatable tubular driving shaft possessing a proximal end and an open distal end, the rotatable tubular driving shaft including a lumen that extends between the proximal end and the open distal end of the rotatable tubular driving shaft;
    a hollow first cutting part fixed to the rotatable tubular driving shaft so that the first cutting part and the rotatable tubular driving shaft rotate together, the first cutting part possessing a distal end portion at which is located an open distal end, the open distal end of the hollow first cutting part including a sharp first cutting blade configured to cut the object when the object and the sharp first cutting blade are brought into contact with one another while the first cutting part is rotating together with the rotatable tubular driving shaft, the sharp first cutting blade extending distally beyond the open distal end of the rotatable tubular driving shaft, the first cutting part possessing an inner surface surrounding an interior of the hollow first cutting part, the interior of the first cutting part communicating with the lumen in the rotatable tubular driving shaft so that pieces of the object which have been cut by the sharp first cutting blade pass through the interior of the first cutting part and enter the lumen in the rotatable tubular driving shaft by way of the open distal end of the rotatable tubular driving shaft; and a second cutting part connected to the rotatable tubular driving shaft so that rotation of the rotatable tubular driving shaft results in rotation of the second cutting blade, the second cutting part including a second cutting blade being positioned in the interior of the hollow first cutting part so that the inner surface of the hollow first cutting part surrounds at least a portion of the second cutting part, the second cutting part possessing a distal end portion at which is located a sharp second cutting blade configured to cut the object when the object and the sharp second cutting blade contact one another while the second cutting part is rotating together with the rotatable tubular driving shaft.

13. The device according to claim 12, wherein the distal end portion of the hollow first cutting part tapers in thickness toward the open distal end of the hollow first cutting part to define a sharp edge constituting the sharp first cutting blade.

14. The device according to claim 12, wherein the distal end portion of the hollow first cutting part includes a plurality of sharp first cutting blades that are circumferentially spaced apart from one another.

15. The device according to claim 14, wherein the distal end portion of the hollow first cutting part includes a plurality of pointed convex portions and concave portions that alternate with one another in a circumferential direction of the first cutting part, each of the pointed convex portions defining one of the sharp first cutting blades.

16. The device according to claim 15, wherein each of the pointed convex portions possesses a radially outwardly facing outer surface part that is curved in a convex shape.

17. The medical device according to claim 12, wherein the sharp second cutting blade possesses a configuration different form the sharp first cutting blade.

18. The medical device according to claim 12, wherein the sharp second blade possesses an inside diameter, the inside diameter of the sharp second blade gradually increasing in a tapering shape toward a distal end of the sharp second blade.

19. The medical device according to claim 12, wherein the sharp first cutting blade possesses a tip end, the sharp second cutting blade possessing a tip end positioned distally beyond the tip end of the sharp first cutting blade of the first cutting part.

20. A treatment method of removing an object of a lesion area in a body lumen, the treatment method comprising:

inserting a medical device into the body lumen, the medical device comprising: a rotatable tubular driving shaft possessing a distal portion at a distal end of the rotatable tubular driving shaft; a cylindrically-shaped first cutting part provided on the distal portion of the driving shaft so that the cylindrically-shaped first cutting part rotates together with the driving shaft, and a second cutting part disposed adjacent the distal end of the rotatable tubular driving shaft and radially inward of the first cutting part;

cutting the object in the body lumen by rotating the first cutting part and the second cutting part through rotation of the driving shaft to produce a cut object, and guiding the cut object to a lumen of the rotating driving shaft;

the cutting of the object in the body lumen by rotating the first cutting part occurring before the cutting by the second cutting part' conveying the cut object in the lumen of the rotating driving shaft toward a proximal end of the rotating driving shaft; and extracting the medical device from the body lumen.

21. The method according to claim 20, further comprising aspirating the lumen of the driving shaft to draw the cut object toward the proximal end of the rotating driving shaft.

* * * * *